United States Patent
Spielmann et al.

(10) Patent No.: US 10,894,766 B2
(45) Date of Patent: Jan. 19, 2021

(54) PROCESS FOR THE PRODUCTION OF ALKANESULFONIC ACIDS

(71) Applicant: BASF SE, Ludwigshafen am Rhein (DE)

(72) Inventors: Jan Spielmann, Ludwigshafen (DE); Juergen Wortmann, Ludwigshafen (DE); Frieder Borgmeier, Ludwigshafen (DE); Michael Zeilinger, Ludwigshafen (DE); Rosario Mazarro Berdonces, Ludwigshafen (DE); Bjoern Kaibel, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/618,283

(22) PCT Filed: May 23, 2018

(86) PCT No.: PCT/EP2018/063455
§ 371 (c)(1),
(2) Date: Nov. 29, 2019

(87) PCT Pub. No.: WO2018/219726
PCT Pub. Date: Dec. 6, 2018

(65) Prior Publication Data
US 2020/0190027 A1     Jun. 18, 2020

(30) Foreign Application Priority Data

May 30, 2017 (EP) .................................. 17173574
May 30, 2017 (EP) .................................. 17173575

(51) Int. Cl.
| C07C 317/04 | (2006.01) |
| C07C 315/06 | (2006.01) |
| C07C 303/06 | (2006.01) |
| C07C 303/44 | (2006.01) |
| C07C 309/04 | (2006.01) |

(52) U.S. Cl.
CPC .......... *C07C 317/04* (2013.01); *C07C 303/06* (2013.01); *C07C 303/44* (2013.01); *C07C 309/04* (2013.01); *C07C 315/06* (2013.01)

(58) Field of Classification Search
CPC ........................... C07C 317/04; C07C 315/06
See application file for complete search history.

(56) References Cited

U.S. PATENT DOCUMENTS

| 2,842,589 | A | 7/1958 | Crowder et al. |
| 4,035,242 | A | 7/1977 | Brandt |
| 4,450,047 | A | 5/1984 | Malzahn |
| 4,938,846 | A | 7/1990 | Comstock et al. |
| 6,337,421 | B1 | 1/2002 | Gancet |
| 2016/0289176 | A1 | 10/2016 | Ott et al. |

FOREIGN PATENT DOCUMENTS

| CN | 1810780 A | 8/2006 |
| DE | 197 43 901 C1 | 4/1999 |
| EP | 0 270 953 A1 | 6/1988 |
| EP | 0 675 107 A1 | 10/1995 |
| GB | 632820 | 12/1949 |
| GB | 1350328 | 4/1974 |
| WO | WO 00/31027 A1 | 6/2000 |
| WO | WO 2005/069751 A2 | 8/2005 |
| WO | WO 2015/071365 A1 | 5/2015 |
| WO | WO 2015/086645 A1 | 6/2015 |

OTHER PUBLICATIONS

Basickes, N. et al., "Radical-Initiated Functionalization of Methane and Ethane in Fuming Sulfuric Acid", Journal of the American Chemical Society, vol. 118, Issue 51, 1996, pp. 13111-13112.
Mukhopadhyay, S. et al., "Catalyzed sulfonation of methane to methanesulfonic acid", Journal of Molecular Catalysis A: Chemical, vol. 211, Issue 1-2, Mar. 15, 2004, pp. 59-65.
International Search Report dated Jul. 31, 2018 in PCT/EP2018/053455 filed May 23, 2018, citing documents AA-AC and AL-AN therein, 3 pages.
U.S. Appl. No. 15/774,722, filed Feb. 26, 2019, US 2018-0327352 A1, Jan Spielmann, et al.
U.S. Appl. No. 15/774,847, filed May 9, 2018, US 2018-0319739 A1, Jan Spielmann, et al.
U.S. Appl. No. 16/605,973, filed Oct. 17, 2019, US 2020-0039927 A1, Juergen Wortmann, et al.
U.S. Appl. No. 16/614,599, filed Nov. 18, 2019, Jan Spielmann, et al.

*Primary Examiner* — Sikarl A Witherspoon
(74) *Attorney, Agent, or Firm* — Oblon, McClelland, Maier & Neustadt, L.L.P.

(57) ABSTRACT

The present invention deals with a process for the production of alkanesulfonic acids, in particular methanesulfonic acid, and a method of purification of the raw products.

24 Claims, 2 Drawing Sheets

PROCESS FOR THE PRODUCTION OF ALKANESULFONIC ACIDS

The present invention deals with a process for the production of alkanesulfonic acids, in particular methanesulfonic acid, and a method of purification of the resulting products.

Methanesulfonic acid ($H_3CSO_3H$, MSA), like other alkanesulfonic acids, is a strong organic acid which is used for a multiplicity of different processes, for example for electroplating processes, in chemical synthesis or in cleaning applications.

MSA can be prepared by various processes.

WO 00/31027 discloses a process for oxidizing dimethyl disulfide with nitric acid to MSA, the oxides of nitrogen formed in the oxidation step are reacted with $O_2$ to yield nitric acid which is being recycled to the process.

The product is purified by distillation in two steps to obtain pure, practically anhydrous alkanesulfonic acid. Water and nitric acid are removed from the crude product in a first distillation column operated at reduced pressure. The bottoms product obtained comprises 1 wt % water and about 1 wt % high boiler, especially sulfuric acid. The separation of the alkanesulfonic acids from high boilers as sulfuric acid is achieved by distillation of the alkanesulfonic acids in a second distillation column yielding purities of greater than 99.5 wt % and sulfuric acid contents of less than 50 ppm at pressures from 0.1 to 20 mbar (abs).

GB-A 1350328 describes the synthesis of alkanesulfonic acids by chlorination of alkyl mercaptans or dialkyldisulfides in aqueous HCl. The product of the reaction is alkanesulfonic acid having a purity from 70 to 85 wt % the remainder being light boilers, mostly water, and traces of high boilers as sulfuric acid. This document describes a two-step process for producing anhydrous methanesulfonic acid. This comprises a first step in which water is distilled off and a second step in which the methanesulfonic acid is distilled out of the bottoms product in a distillation column and obtained at the top of the column with a purity greater than 99.5 wt %.

CN-A 1810780 describes the synthesis of methanesulfonic acid by reaction of ammonium sulfite with dimethyl sulfate. This affords ammonium methylsulfonate and ammonium sulfate. Addition of calcium hydroxide forms soluble calcium methylsulfonate and insoluble calcium sulfate which may be removed easily. Sulfuric acid is added to liberate methanesulfonic acid and once again form and precipitate calcium sulfate. The aqueous solution formed is initially subjected to distillation to remove water and then subjected to distillation under reduced pressure to obtain methanesulfonic acid. No further details are given for the purification of MSA by distillation.

DE-C 197 43 901 describes the synthesis of methanesulfonic acid by reaction of sulfite ions with dimethyl sulfate. These sulfite ions are reacted in an aqueous system at elevated temperature and exposed to a strong acid. Sulfate is formed as a byproduct, for example in the form of sodium sulfate. Purification of the acid could be done for example by distillation, but no details are given for this purification step.

EP-A 0 675 107 describes a process for continuous production of alkanesulfonyl chloride (ASC) or alkanesulfonic acid (ASA) by reacting an alkane mercaptan or a dialkanedisulfide with chlorine in aqueous hydrochloric acid at elevated pressure. Hydrogen chloride (HCl) and other low boilers not condensable under the process conditions are desorbed after being depressurized to atmospheric or sub-atmospheric pressure. ASC is produced at a preferred temperature range of from 10° C. to 35° C. ASA is obtained from ASC by hydrolysis at temperatures of from greater than 80° C. to 135° C. in the presence of water. The purification of ASC and/or ASA is also carried out with a vapor stripper for example, residual ASC also being hydrolyzed therein. The process leads to MSA which, despite purification, still comprises small amounts of chlorine-containing compounds, for example chloromethanesulfonic acid.

The removal of water from aqueous methanesulfonic acid by evaporation of the water in a falling film evaporator at reduced pressure is described in U.S. Pat. No. 4,450,047. Water is drawn off overhead and a product stream comprising more than 99.5 wt % methanesulfonic acid is obtained. The content of Methylmethanesulfonate (MMS, $CH_3$—$SO_2$—$OCH_3$) is analyzed to be less than 1 ppm. Sulfuric acid could not be detected in the purified MSA.

U.S. Pat. No. 4,938,846 discloses the removal of water from aqueous methanesulfonic acid by evaporation of the water in two falling-film evaporators arranged in series and both operated at reduced pressure.

U.S. Pat. No. 4,035,242 discloses a process where aqueous methanesulfonic acid is purified in a two-step distillation process. In the first distillation column a large part of the water is removed as a low boiler at reduced pressure. The bottoms product comprising methanesulfonic acid, light boilers as water and high boilers as sulfuric acid is evaporated and separated in a second rectification column at reduced pressure to obtain the methanesulfonic acid with a purity of 98.89 wt-%. The water content of the resulting MSA is <2 wt-%. The content of Methylmethanesulfonate is described to be 0.08 wt % on average, that of sulfuric acid to be 0.46 wt %.

U.S. Pat. No. 6,337,421 discloses the removal of sulfuric acid from methanesulfonic acid using basic anion exchange resins. Other processes of removing sulfuric acid are also described, for example distillation or fractionating crystallization and also separation by nanofiltration, but according to U.S. Pat. No. 6,337,421, none of these methods give satisfactory results.

WO-A 2005/069751 describes a methanation process which is the synthesis of methanesulfonic acid from sulfur trioxide and methane via a free-radical chain reaction with for example Marshall's acid as free-radical initiator in a methanation reactor. In this synthesis, anhydrous methanesulfonic acid is formed, but no information is given about purification.

WO 2015/071365 A1 discloses a process for the manufacture of alkanesulfonic acids (e.g. MSA) from sulfur trioxide (SO3) and alkanes (e. g. methane) by using peroxides. It is assumed that the reaction follows a radical mechanism. The product of this production process is mostly free of water. However, it may comprise e.g. sulfur trioxide, methane, methanesulfonic acid anhydride and/or methanedisulfonic acid (methionic acid, $CH_2(SO_3H)_2$) and significant amounts of sulfuric acid. The resulting product is processed by distillation; however, no details of the workup and distillation of the alkanesulfonic acids are mentioned.

WO-A 2015/086645 describes the production of alkanesulfonic acid by oxidation of dialkyldisulfides in the presence of catalytic amounts of nitrogen oxides. The nitrogen oxides are regenerated with oxygen-enriched air for example. The reaction products could be subsequently freed of low and high boilers via distillation in two distillation columns. The published process yields alkanesulfonic acid without any indication on the distillation conditions applied, on the resulting product composition or its specification.

Other side-products may be generated when the distillation is performed under harsh conditions, in particular at high temperatures.

For the purification of aqueous MSA it is known that Methylmethanesulfonate (MMS) may form at high temperatures, see e.g. U.S. Pat. No. 4,450,047 or 4,035,242, but no details are given with regards to building rates, potential thresholds for its formation with regard to temperature etc.

For anhydrous conditions, the formation of Methylmethanesulfonate has not been described so far.

It is known that $SO_3$ reacts with MSA at elevated temperatures of 100 to 150° C. and leads to the formation of methanedisulfonic acid (methionic acid, $CH_2(SO_3H)_2$). Thus, when the distillation is done at high temperatures, undesired by-products may be formed by conversion of $SO_3$ with the MSA product, for example $CH_2(SO_3H)_2$ and/or $CH_3SO_3CH_3$ (MMS) and/or $CH_3SO_2OSO_2CH_3$ (methanesulfonic acid anhydride, MSAA), leading to a decreased yield for MSA.

U.S. Pat. No. 2,842,589 (Allied 1956) describes that methionic acid is obtained from the reaction of MSA with sulfur trioxide at temperatures in the range of 100° to 150° C. As mentioned, temperatures like this are also common in the distillation of a crude MSA product to generate pure MSA. According to Mukhopadhyay et al., MSA may be oxidized to Methylbisulfate $CH_3OSO_3H$ by using $SO_3$ at a temperature of 130° C. in the absence of a catalyst or in the presence of metal salts (S. Mukhopadhyay, A. T. Bell, J. of Molecular Catalysis A: Chemical 211 (2004), 59-65). Mukhopadhyay et al. describe metal catalyzed reactions, in particular Hg catalyzed reactions. It is postulated that $MeOSO_3H$ is generated without a metal.

A. Sen et al. describe the formation of Methylbisulfate as side product when reacting methane and SO3 at 90° C. (N. Basickes, T. E. Hogan, A. Sen, J. Am. Chem. Soc. 118 (1996), 13111-13112).

Furthermore, $SO_3$ reacts with MSA and forms Methanedisulfonic acid ($CH_2(SO_3H)_2$, Methionic acid) and MSA anhydride plus sulfuric acid. The respective reactions are equilibrium reactions. Therefore, as the reactions are reversible, distillation (and/or stripping) of $SO_3$ at higher temperatures leads to an increased concentration of undesired MSA anhydride.

Generally, distillation processes in a manufacturing process for MSA described so far mainly serve the purpose of removing water.

For the applications listed earlier the purified MSA needs to have a low content of sulfuric acid and a low content of methylmethanesulfonate. E.g. in electroplating applications a low sulfuric acid content is important to avoid precipitation of metal sulfates on the metal substrate in the plating process. In chemical synthesis, e.g. in esterification reactions, sulfuric acid promotes corrosion whereas corrosion of MSA with a very low sulfuric acid content is reduced. Methylmethanesulfonate is carcinogenic. The content of methylmethanesulfonate in purified MSA therefore should be very low or zero, e.g. below 1000 ppm, to avoid handling of carcinogenic compounds or mixtures.

A distillation process for MSA generated in an anhydrous (water-free) environment has not been described so far. Typical low boilers in an anhydrous environment comprise e.g. methane, SO3, MSA anhydride, methylmethanesulfonate, and even MSA could be considered a low boiler in such an environment: MSA is light boiler compared to sulfuric acid, but it has a high boiling point itself. Typical high boilers comprise e.g. sulfuric acid, methionic acid and possibly polysulfuric acids generated by addition of SO3 to sulfuric acid and/or to MSA. One challenge for a distillation of such a feed is to separate MSA from high boilers, especially from sulfuric acid, with high MSA yields while at the same time avoiding or minimizing the formation of methylmethanesulfonate in the course of the distillation (additional methylmethanesulfonate might be introduced into the distillation step as side product from the MSA synthesis step when reacting methane and SO3. Methylmethanesulfonate formation in the synthesis step, i.e. prior to distillation, should be minimized as well but is not in the focus of this invention. However, it even emphasizes the need to reduce the formation of additional methylmethanesulfonate in the course of the distillation by thermal stress).

As a result of the different composition of MSA generated in an anhydrous environment the task for the purification step, namely for the distillation, is different from purification of MSA produced in an aqueous environment with typically a very low content of high boilers as sulfuric acid.

In other words, this invention needs to provide a solution to several problems at the same time. MSA needs to be separated from significant amounts of sulfuric acid to achieve low sulfate contents in the final product while at the same time avoiding or at least reducing the formation of methylmethanesulfonate. Another aspect is that MSA purification achieves high MSA high yields. Yet another aspect is that the separation of MSA and sulfuric acid requires significant amounts of energy. The overall consumption of energy should be kept to a minimum.

Yet another aspect is that the formation of decomposition products as Methylmethanesulfonate needs to be avoided as carcinogenic byproducts are not wanted. In another aspect their formation needs to be minimized to obtain high yields and don't add further complexity to the purification steps.

Problems may therefore arise in the manufacture of alkanesulfonic acids from the corresponding alkane and sulfur trioxide, for example MSA from methane and sulfur trioxide, when the subsequent distillation is done in one step only (for example in one single distillation column), wherein the low-boiling components of the reaction mixture are removed at the column head and MSA is removed at a side discharge. High-boiling compounds as sulfuric acid remain at the bottom of the column and are removed from the process via bottom discharge (also called "bottom purge" or just "purge"). In a process like this, to achieve a high separation performance and at the same time high MSA yields the temperatures in the sump and in the column packings must be relatively high, thus the formation of by-products as mentioned above is very likely, which may result in a reduced yield of the desired product and an increased amount of impurities.

Additional measures in such a set-up could be to either increase the purge, i.e. the amount of MSA removed from the system along with impurities. Depending on the impurity this means to either increase the low boiler purge stream at the upper part of a distillation column or to increase the high boiler purge stream in the lower part of a distillation column or both. However, this usually results in lower purification yields. Another option to achieve high MSA purities is by increasing the separation performance in the distillation step (more "theoretical plates") which, however, increases both the pressure drop over the column (i.e. higher bottom temperatures and thus higher thermals stress on the product) and the residence time of the product in the column. Then the thermal stress on the product increases resulting in higher decomposition rates, and finally the energy demand increases as well.

Neither the set-up of a single column nor the standard measures to improve the performance of the purification are sufficient, neither for the product quality nor for the process economics, especially not for its yield and energy demand.

There is no disclosure in the art of a purification process (for example a distillation process) which could solve the problems mentioned above in the synthesis of an alkanesulfonic acid from the corresponding alkane and sulfur trioxide, e.g. MSA from methane and sulfur trioxide.

It was therefore an object of the present invention to provide a process for the production and/or purification of alkanesulfonic acids from sulfur trioxide and the corresponding alkane, in particular methanesulfonic acid from sulfur trioxide and methane, with high yield which avoids or at least reduces the generation of unwanted by-products, in particular in the distillation step, thus leading to MSA with a higher purity and/or greater yield. Another aspect of the present invention is to provide a process where the amount of energy for the distillation is reduced.

The challenges listed above, the reduction of sulfuric acid in the resulting MSA despite high sulfuric acid concentrations in the distillation feed, along with the formation of decomposition products as methylmethanesulfonate with high temperatures, could now surprisingly be overcome by using a specific multi-step purification process, especially a two-step or a three-step distillation process. MSA with a high purity of >99% and yields after distillation of >80%, preferably of >85%, more preferably >90% may be achieved. At the same time the formation of by-products could be minimized.

Furthermore, it was found that the energy input for distillation could be reduced.

Thus, in one aspect, the subject of the current invention is a process for preparing alkanesulfonic acids from sulfur trioxide and an alkane, wherein the produced raw alkane sulfonic acid is purified in a distillation process comprising at least two steps.

In another aspect, the subject of the current invention is a process for purification of raw alkanesulfonic acids manufactured from sulfur trioxide and an alkane, wherein the raw alkane sulfonic acid is purified in a distillation process comprising at least two steps (as described in more detail below). In another aspect, the invention relates to a process for purifying reaction mixtures comprising raw alkanesulfonic acids, preferably raw methanesulfonic acid, by subjecting the reaction mixture to at least two distillation steps.

The process for preparing (raw) alkanesulfonic acids from sulfur trioxide and an alkane may be performed, for example, as described in BASF unpublished patent application no. EP 17173575.6. For example, the raw alkanesulfonic acid may be manufactured as follows: reaction of a radical initiator composition with methane and sulfur trioxide comprising the steps:

a) Preparation of the initiator composition by reacting aqueous hydrogen peroxide with the components methane sulfonic acid and methane sulfonic acid anhydride, and b) Reaction of initiator composition from step a) with sulfur trioxide and methane to form methane sulfonic acid.

More specifically, one subject of the current invention is a process for preparing alkanesulfonic acids from sulfur trioxide and an alkane, wherein the produced raw alkane sulfonic acid is purified in a distillation process comprising at least two steps, and wherein a distillation set-up is used comprising (i) at least one distillation column with high separation performance (main distillation) and (ii) at least one additional distillation columns, either before and/or after the main distillation column, each with a separation performance not matching that of the main distillation column (pre-distillation and/or post-distillation, respectively).

The column with the high separation performance is characterized by a higher number of theoretical plates than the at least one additional distillation column.

In the context of this invention, the terms "high separation performance", "high distillation performance" or "main distillation" refer to the number of theoretical plates of a column. Generally spoken the more theoretical plates the better the separation performance. In other words, the more theoretical plates a column has, either the more complex product mixtures can be separated or alternatively product mixtures with compounds with very similar distillation behavior (e.g. boiling point) can be separated, and the less impurities remain in the main fraction.

A theoretical plate can be technically realized e.g. by building a real plate into a column (fictive example: one theoretical plate corresponds to one real plate) or by increasing the height of the packing proportionally to the number of theoretical plates (fictive example: one theoretical plate corresponds to 50 cm height of the packing, two theoretical plates correspond to a height of 100 cm etc.). In the context of this invention the main fraction is the alkanesulfonic acid, particularly methanesulfonic acid.

In the following a purification set-up is described using methanesulfonic as example for an alkanesulfonic acid and methane as alkane, but the set-up could be used in the same way to purify alkanesulfonic acids with 1 to 4 carbon atoms in the chain and the corresponding C1 to C4 alkanes.

The liquid mixture entering the first purification apparatus (e. g. a distillation column) contains a high percentage of product (MSA), but also some unreacted methane and sulfur trioxide, along with sulfuric acid and other compounds such as methanesulfonic acid anhydride, methionic acid, methylbisulfate etc. This first purification step is typically realized in a distillation column. Alternatively it can be done in a reaction vessel or other devices as long as the reaction conditions given below can be met.

The inventive solution involves keeping the maximum temperatures in the distillation set-up low and the residence time of the alkanesulfonic acid, e.g. MSA, short while at the same time achieving a good purification effect for the alkanesulfonic acid. This is achieved with a distillation set-up which provides one distillation column with high separation performance (main distillation) and one or two additional distillation columns, either before and/or after the main distillation column, with a separation performance not matching that of the main distillation column (pre-distillation and/or post-distillation, respectively). The pressure drop in the main distillation column is the same or higher than the pressure drop in the other one or two columns, a higher pressure drop is preferred. This helps to keep the temperatures at the bottom of the columns low (the higher the pressure drop the higher will be the temperatures to partially evaporate the bottom mixture and the higher the respective thermal stress on this mixture, especially on MSA in the mixture). At the same time the residence times are reduced compared to a single-step distillation or compared to operating the additional columns at the same pressure drop as the main distillation column. The one to two additional columns are interconnected to the main distillation in a way that at least the liquid phases, but optionally also the gas phases are integral part of the product loops of the main distillation column. Prior to the distillation columns as such the raw-MSA stream coming from the synthesis step can be decompressed in an expansion or flash vessel. Such a flash vessel is considered part of the purification set-up.

DETAILED DESCRIPTION OF THE INVENTION

In the following the invention is described in more detail. Schematic drawings of the inventive set-ups for the distillation can be found in FIGS. 1-4.

In the following paragraphs an exemplary two-column set-up is described.

The raw-MSA generated in a synthesis step as described e.g. in WO 2005/069751 A1 or in WO 2015/071365 A1 is usually sent to an expansion vessel prior to distillation, also called flash or flash vessel. It could be flashed directly into the first distillation column, but normally it is avoided to feed this raw-MSA stream directly from the synthesis unit into the purification unit as the pressure levels differ significantly (ca. 50-100 bar in the synthesis unit compared to 0.1-30 mbar in the purification unit). The reaction mixture can easily be depressurized to normal pressure in the flash and gases dissolved in the mixture under the pressure of the reaction, e.g. methane, will at least partially degas from the mixture. This gas evolving from the liquid could e.g. be recycled to the reactor, at least partially, or sent to a treatment facility or used for other purposes, e.g. to generate heat. The depressurization could be done in one or in several steps. If the depressurization is carried out in more than one step, these steps could be operated at similar pressure levels, but preferred they are operated at stepwise decreasing pressure levels until a pressure level close to or at that of the first distillation column is reached.

The depressurized raw-MSA is sent to the first distillation column at about normal pressure, but the pressure can also be slightly above or below normal pressure, e.g. between 0.3 to 5 bar absolute (bara) or between 0.5 and 2.0 bara. It can enter the column at a side feed, a bottom feed or a top feed. To enter the first column at a side feed is preferred. In a two-column set-up this first column does the main separation. It is typically equipped with column internals, e.g. packings like loose or structured packings (especially high performance packings displaying a particularly low pressure drop of 10 to 30% less compared to standard packings), to increase the performance of the separation. These internals generate a certain pressure drop between the top and the bottom of the column and should be designed to keep the pressure drop to a minimum, e.g. below 30 mbar, preferred below 20 mbar and even more preferred below 15 mbar, 10 mbar or 5 mbar. The packings can be made from stainless steel (e.g. Hastelloy types as C22), from special polymers (e.g. native PFA or PTFE), from ceramics (e.g. Si—Al-based ceramics or Si—N-based ceramics; the ceramic can be glazed with the same or a similar material) or from glass-lined material (e.g. glass-lined steel). Light boilers as e.g. methane, SO3, MSA anhydride or methylmethanesulfonate are purged from the system at the head of this column, more precisely via the condenser on top of the column. Purified MSA is removed from the column via side discharge, the side discharge being located in the upper half of the first column. The high boilers are withdrawn at the bottom of the column and sent to the second column (post distillation to improve separation of MSA from high-boilers). The high boilers enter the second column at a side feed or a bottom feed. Preferably they enter the column at a side feed located in the lower half of the column. The second column is operated with a pressure drop which is the same or below the pressure drop in the first column. A lower pressure drop compared to the main distillation column is preferred. This is achieved e.g. by using internals which generate an especially low pressure drop (below 20 mbar, preferably below 10 mbar or even below 6 or 3 mbar), or by using less internals of the same type as in the first column or even using no internals at all. High boilers as e.g. sulfuric acid, methionic acid or polysulfuric acid are purged from the system via bottom outlet of the second column. This purge typically contains sulfuric acid and MSA as main compounds and could be sent to a waste treatment plant, alternatively at least part of it could be recycled to the synthesis step, or the purge might be used for other purposes. MSA and possibly last traces of low boilers are condensed at the head of the second column, more precisely at a condenser on top of the second column, and recycled to the first distillation column. This stream could be fed into the lower half of the first column or mixed with the product mixture circulating at the bottom of the first column. Feeding the condensed light boilers of the second column via feed located in the lower half into the first column is preferred. Column 2 can be realized as column or as a simple vessel or another type of equipment meeting the required functionality.

The energy required for evaporating the liquid streams at the bottom of columns 1 and 2 is conveniently provided either by a naturally circulating evaporator or by a forced circulation evaporator ("Zwangsumlaufverdampfer") with a heat exchanger (evaporator) and a pump which makes the liquid stream circulate. A set-up with forced circulation evaporator is preferred.

As mentioned above, FIG. 3 shows a schematic drawing of a three-column set-up for the purification of alkanesulfonic acids by distillation according to the invention, which is particularly suitable for the purification of MSA.

In the following paragraphs an exemplary three-column set-up is described.

The raw-MSA generated in a synthesis step as described e.g. in WO 2005/069751 A1 or in WO 2015/071365 A1 is usually sent to an expansion vessel prior to distillation, also called flash or flash vessel. It could be flashed directly into the first distillation column, but normally it is avoided to feed this raw-MSA stream directly from the synthesis unit into the purification unit as the pressure levels differ significantly (ca. 50-100 bar in the synthesis unit compared to 0.1-30 mbar in the purification unit). The reaction mixture can easily be depressurized to normal pressure in the flash and gases dissolved in the mixture under the pressure of the reaction, e.g. methane, will at least partially degas from the mixture. This gas evolving from the liquid could e.g. be recycled to the reactor, at least partially, or sent to a treatment facility or used for other purposes, e.g. to generate heat. The depressurization could be done in one or in several steps. If the depressurization is carried out in more than one step, these steps could be operated at similar pressure levels, but preferred they are operated at stepwise decreasing pressure levels until a pressure level close to or at that of the first distillation column is reached.

The depressurized raw-MSA is sent to the first distillation column at about normal pressure, but the pressure can also be slightly above or below normal pressure, e.g. between 0.3 to 5 bar absolute (bara) or between 0.5 and 2.0 bara. The depressurized raw-MSA enters the first column at a side feed or it is fed into the loop circulating the liquid at the bottom of the first column. Feeding the depressurized MSA at a side feed of the first column is preferred. In a three-column set-up this first column serves to separate MSA and light boilers from high boilers (pre-distillation). By far the largest portion of MSA and low boilers as e.g. methane, SO3, MSA anhydride or methylmethanesulfonate leave the first column at the head of the column, more precisely via the condenser on top of the column. As the separating performance of the first column is not as high as that of the main distillation (column 2) and as therefore separation of MSA and low boilers on the one hand and high boilers on the other hand in this first column is not complete this stream may still contain small amounts of high boilers, e.g. <5 wt-%, <3 wt-%, <1 wt-% or even <0.5 wt-% or <0.1 wt-%. High boilers as e.g. sulfuric acid, methionic acid or polysulfuric acid—stripped of basically all low boilers—leave the column at the bottom. This bottom stream (purge) typically contains sulfuric acid and MSA as main compounds and could be sent to a waste treatment plant, alternatively at least part of it could be recycled to the synthesis step (either to the synthesis of the radical starter or to the synthesis of MSA), or the purge might be used for other purposes. MSA and light boilers are sent to a phase separator which at least partially separates MSA from other light boilers by condensation of MSA. This phase separator can be a simple vessel, a vessel with additional internal or external cooling functionality, e.g. outer or inner heating coils, or a heat exchanger to condense MSA more or less quantitatively (e.g. >98.0 wt-%, preferred >99.0 wt-%, most preferred >99.5 wt-% of MSA being condensed) or a combination of the equipment listed above. Light boilers which don't condense in the phase separator are purged from the system.

The condensed MSA including some remaining light boilers and small amounts of high boilers are sent to the second distillation column. This stream can either enter the column at a side feed in the lower half of the column or it can be fed into the liquid stream circulating at the bottom of the column. Feeding this stream into column 2 at a side feed in the lower half of the column is preferred. The main separation to purify MSA is done in this second column. It finally removes light boilers, which are purged from the system at the top of the column, from MSA, more precisely at the condenser on top of the column. At the bottom of the column the high boilers are separated from MSA and removed from the system by sending at least part of the circulating liquid back to column one (the other part of this stream is sent to the forced circulation evaporator). This stream can enter the first column at the top, at a side feed or at the bottom. Feeding this stream into the upper half of column 1 is preferred. Another option is to purge a fraction of this stream from the bottom of column 2 and handle it as described for the bottom purge of column 1.

To further intensify the purification performance the second column is closely connected to a third column (post-distillation to improve separation of MSA from high-boilers), both via the upper part of the column (rectification section) and via the lower part of column 2 (stripping section). This interconnection follows a set-up which is also called dividing wall set-up, realized in two columns rather than in one column for reasons of easier and more flexible operation. This set-up could also be realized in one column.

Condensate from the rectification section of column 2 is fed into column 3 at the top or the upper half of column 3. At the same time evaporated MSA, possibly containing traces of light boilers, leaves column 3 at the top of the column, more precisely via the condenser on top of the column, and re-enters column 2 at the rectification section. The final product, purified MSA, leaves column 3 via side discharge located in the rectification section of the column. Evaporated MSA from the stripping section of column 2 enters column 3 at the bottom or is fed via side feed into column 3. Condensate in column 3, namely MSA with traces of high boilers, leaves column 3 at the bottom and re-enters column 2 at the stripping section.

The second column is typically equipped with column internals, e.g. packings like loose or structured packings (especially high performance packings), to increase the performance of the separation. These internals generate a certain pressure drop between the top and the bottom of the column and should be designed to keep the pressure drop to a minimum, e.g. below 30 mbar, preferred below 20 mbar and even more preferred below 15 mbar, 10 mbar or 5 mbar. The packings—and this holds for all columns used in the purification set-up—can be made from stainless steel (e.g. Hastelloy types as C22), from special polymers (e.g. native PFA or PTFE), from ceramics (e.g. Si—Al-based ceramics or Si—N-based ceramics; the ceramic can be glazed with the same or a similar material) or from glass-lined material (e.g. glass-lined steel). The first and the third column are operated with a pressure drop which is the same or below the pressure drop in the second column (main distillation column). A lower pressure drop compared to the main distillation column is preferred. This is achieved e.g. by using internals which generate an especially low pressure drop (below 20 mbar, preferably below 10 mbar or even below 6 or 3 mbar), or by using less internals of the same type as in the first column or even using no internals at all. In this set-up the pressure drop in column 3 is not only defined by the power of the vacuum unit but also by the decision at which height of column 2 the connections between column 3 and column 2 are positioned, to feed MSA from column 2 to column 3 and to return MSA to column 2, respectively. As the internals of column 2 generate some pressure drop—each theoretical tray contributing to the total pressure drop in column 2—the pressure at the head of column 3 is higher than at the top of column 2, and the pressure at the bottom of column 3 is lower than the pressure at the bottom of column 2.

Columns 1 and 3 can be realized as column or as a simple vessel or as piece or pieces of pipeline or as another type of equipment meeting the required functionality.

The energy required for evaporating the liquid streams at the bottom of columns 1 and 2 is conveniently provided either by a naturally circulating evaporator or by a forced circulation evaporator ("Zwangsumlaufverdampfer") with a heat exchanger (evaporator) and a pump which makes the liquid stream circulate. A set-up with forced circulation evaporator is preferred. Due to the close interconnection of columns 2 and 3, column 3 does not necessarily require additional energy to heat the incoming gas stream or to re-evaporate the condensate in column 3, but it can optionally be provided in the same way as in columns 1 and 2.

In the three-step distillation a condensation step after the first distillation step (column 1) is recommended as described above. Such a step facilitates control of the vacuum at the head of columns 1 and 2 (indirectly also of column 3) and thus makes it easier to control the pressure of the gas phase at the bottom of the column right above the liquid at the phase boundary between gas and liquid. Alternatively a three-column set-up could be operated without this condensation step. The advantage of avoiding an additional condensation and subsequent re-evaporation step might energetically be overcompensated by higher bottom temperatures in the distillation steps. High temperatures should be avoided, though, to reduce decomposition of the alkanesulfonic acid, especially of MSA. Operating the system with a condensation step after the first distillation step is preferred.

If the MSA purity is already sufficient after the second distillation column, the third column can be omitted and the final product is removed from column 2 via side discharge in the rectification section of the column.

Depending on the plant capacity all columns in the process according to the invention can be realized in one column or in more than one column operated in parallel. In other words, the same distillation functionality can be handled in one column or split into two or more columns.

Stripping by addition of a gaseous carrier is being regarded as a distillative or evaporative process.

To obtain best results for the purified MSA not only with regards to a low content of high boilers in the purified MSA, especially of sulfuric acid, but also with regards to a low content of decomposition products as e.g. methylmethanesulfonate, it is necessary to keep the temperatures in the purification unit low, especially at the bottom of the columns. Careful investigations have shown that decomposition of MSA to methylmethanesulfonate and other side compounds accelerates if temperatures reach 200° C. or more. Temperatures in the purification step should therefore be controlled in a way that they remain at 200° C. max or below 200° C. Keeping temperatures below 200° C. is preferred. Otherwise the content of methylmethanesulfonate and other impurities in the purified MSA will quickly increase and the MSA yield is reduced by increasing decomposition, especially but not only in the sump of the column including the liquid loop with pipes, pump and heat exchanger.

On the one hand the content of e.g. methylmethanesulfonate in the purified MSA is dependent on the temperature. On the other hand it is dependent on the residence time of MSA in the system at a given temperature, i.e. on the hold-up in the system. To reduce the formation of e.g. methylmethanesulfonate the hold-up of MSA in each of the at least two distillation steps should be small so that the residence time of MSA can be kept short, e.g. <5.0 h, preferred <3.0 h and even more preferred <2.0 h or <1.0 h or any value between these values or ranges thereof. The residence time could also be <0.8 h, <0.6 h, <0.5 h, <0.4 h, <0.3 h, <0.2 h or <0.1 h. The residence time in this invention is focused on the residence time in the liquid phase at the bottom of the column and is estimated by dividing the MSA hold-up at the bottom of the column by the MSA mass flow to the respective column (not the volume flow of the total feed to the distillation column incl. e.g. sulfuric acid). The focus on the liquid phase at the bottom of the column only—rather than the total of liquid phase and gas phase—is a simplification which is justified (i) because the heat exchangers deliver heat into the bottom of the column so that this is the spot where temperatures are highest, (ii) because the temperature decreases upwards over the column profile, i.e. over the height of the column and (iii) because decomposition in the gas phase is less likely than in the liquid phase since the density of the molecules is much lower than in the liquid phase. The liquid hold-up at the bottom of the column comprises e.g. the volume occupied by MSA in the liquid in the sump of the column, in the pipelines circulating the mixture in the sump from the sump via pump via heat exchanger(s) back to the sump, in the heat exchanger(s) and the pump circulating the liquid in the sump). The MSA hold-up is defined as the volume of the hold-up as described above multiplied by the MSA-concentration in this volume.

$$\text{residence time } (v_r \text{ in h}) = \frac{\text{Hold-up } MSA(m_{MSA} \text{ in kg})}{MSA \text{ feed to column } (\dot{m}_{MSA} \text{ in kg/h})}$$

$$\text{Hold-up } MSA(m_{MSA} \text{ in kg}) = \text{concentration } MSA(c_{MSA} \text{ in wt-\%}) \times$$
$$\text{total liquid hold-up at bottom of column } (m_{total} \text{ in kg})$$

This can be achieved by several measures, each being relevant by itself, but also in combination with one or all other measures quoted below. Such measures comprise (i) keeping the pressure drop in the columns low by using column internals or packings generating only a minimum pressure drop as described above (especially high performance packings characterized by a pressure drop of 10 to 30% less compared to standard packings), (ii) interconnecting the columns with pipelines as short as possible, (iii) allowing sufficient pipe diameter for interconnections in the gas phase, (iv) using columns with a reduced sump volume ("eingezogener Sumpf"), (v) using columns with a split sump ("geteilter Sumpf"), (vi) keeping the level of the liquid in the sump low, (vii) using evaporators with reduced hold-up, (viii) in general keeping the hold-up of the liquid at the bottom of the column small incl. column sump, evaporator, piping, pumps etc. (ix) To apply a stronger vacuum machine is yet another option. However, this increases the energy demand and is therefore not preferred.

When using columns with a reduced sump volume ("eingezogener Sumpf") in this invention this is to be understood in a sense that the diameter of the column in the sump is reduced compared to the diameter of the column in the stripping section (i.e. the lower part of the column directly above the sump). In this invention the column diameter is always the inner diameter of the column. Of course the diameter of the column above the sump can vary over the height of the column, namely in the stripping section and/or the rectification section, but in this invention the focus is on the diameter in the sump relative to the diameter immediately following above the sump (typically the stripping section or part of the stripping section of the column). The ratio of the diameter of the sump compared to the diameter of the column immediately above the sump can be in the range from 0.2 to 0.99, preferred from 0.5 to 0.95 m/m and most preferred from 0.6 to 0.9 and is calculated as follows $$\text{Ratio}_{sump/column} = \text{inner diameter}_{\text{"reduced sump volume"}} \text{[mm]}/\text{inner diameter}_{column\ immediately\ above\ sump} \text{[mm]}$$

The multiplication of "hold-up" with "formation rate MMS at a given temperature" should not yield MMS contents in the purified MSA higher than 1000 ppm, preferred not higher than 700 ppm or 500 ppm, more preferred not higher than 300 ppm or 200 ppm, and most preferred not higher than 150 ppm or even 100 ppm. The focus of the description about formation of side products is on MMS, but a person skilled in the art will be aware that formation of other decomposition products as e.g. methylbisulfate or methionic acid has the same negative effect on purification yields, purity of the finals product, energy consumption etc. It will therefore be clear that measures taken to reduce the formation of MMS (i.e. the decomposition of MSA to MMS)

also help to reduce or even totally avoid the formation of other decomposition products as well.

According to the inventive process, all distillation steps are operated at a bottom temperature of 130° to 200° C. (preferably 150° to 200° C., more preferably 170° to 195° C. or 160° to 190° C.) and a pressure at the top of the columns of 0.1 to 30 mbar (preferably 1 to 20 mbar, more preferably 3 to 15 mbar or 5 to 10 mbar).

In a distillation set-up according to the invention MSA purities of >98 wt-%, even >98.5 wt-% and preferred >99 wt-% and more can be achieved, e.g. >99.1 wt-% or >99.3 wt-% or >99.5 wt-% or >99.7 wt-% or >99.8 wt-%. MSA yields in such a distillation set-up typically are >80 wt-%, preferred >85 wt-% or >87 wt-% and even more preferred >90 wt-% or >95 wt-%. The sulfuric acid content in the purified MSA is less than 100 ppm, preferred less than 50 ppm and even more preferred less than 30 ppm, 20 ppm or 10 ppm. This value can be given as sulfuric acid or as sulfate concentration, both parameters are considered equivalent in this application. The content of methylmethanesulfonate (MMS) in the purified MSA is less than 1000 ppm or less than 500 ppm. In a preferred mode the MMS content in the purified MSA is less than 300 ppm and even more preferred less than 200 ppm or below 100 ppm.

One object of the invention therefore is a process for preparing alkanesulfonic acids from sulfur trioxide and an alkane in the presence of a radical starter, wherein the produced raw alkane sulfonic acid is purified in a distillation process comprising at least two steps.

Further objects of the present invention include an alkanesulfonic acid, obtainable by the inventive process, and the use of an alkanesulfonic acid, obtainable by the inventive process, e.g. for cleaning applications, in chemical synthesis or in an electroplating process.

One object of the invention is also to provide a process with low energy consumption while at the same time generating a very pure product MSA.

Peroxides can react as explosives. A further object of the present invention therefore is to provide means to prevent accumulation of peroxides in the process and in the purified MSA by destroying peroxide compounds in the course of the distillation, i.e. without installing dedicated equipment for destroying peroxides prior to or after distillation.

Another object of this invention is to recycle MSA anhydride. To further reduce the loss of MSA thus improving the MSA yield this MSA anhydride can either be directly hydrolyzed by adding equimolar amounts of water (e.g. into a separate loop or into the condensate at the heat exchanger on top of the column), or it can be separated from the light boilers, e.g. via formation of crystalline MSA anhydride which is poorly soluble in water or by an additional distillation step. This separated MSA Anhydride can either be hydrolyzed to MSA and then be combined with the MSA from the distillation. Another use would be as anhydride in the synthesis of the radical starter solution. It is also object of this invention to provide means to generate a purified MSA which still contains small amounts of MSA anhydride, e.g. <2.0 wt-%, preferred smaller 1.0 wt-% or most preferred <0.5 wt-%.

Further objects and preferred embodiments of the present invention are also defined by the independent and dependent claims.

In an embodiment of the invention, at least a part of the bottom fraction of the MSA distillation is not purged from the system but at least partially recycled to the synthesis step of the radical starter solution or to the synthesis step of the MSA synthesis with $CH_4$ and $SO_3$.

Stripping with an inert gas, like nitrogen or argon, may also be performed in one or more of the distillation steps in an embodiment of the inventive process, in order to improve distillation results and/or shorten distillation times.

Preferably, the inventive at least two-step distillation process is performed in at least two separate distillation columns or alternative equipment meeting the same functionality, e.g. perform the first distillation step in a simple vessel under the conditions given above. This is preferable inter alia because a preferred embodiment of the inventive process for the synthesis of MSA is a continuous process.

This same holds true if the inventive process is realized as three-step distillation process, where the distillation can be carried out in three separate columns or alternative equipment meeting the same functionality, e.g. perform the first and/or the last distillation step as described above in a simple vessel under the conditions given above.

The synthesis of the raw alkanesulfonic acids, for example raw methanesulfonic acid, may e. g. be done in accordance with the disclosure of WO 2015/071365 A1, by using sulfur trioxide and an alkane (preferably methane) as well as a radical starter as educts.

The generation of a suitable radical starter may also be performed, for example, in accordance with the teachings of WO 2015/071365 A1 or other publications mentioned above.

One specific embodiment of the inventive process comprises a process for preparing alkanesulfonic acids (e.g. MSA) from sulfur trioxide and the corresponding alkane (e.g. methane), wherein sulfur trioxide, the alkane (e.g. methane) and dialkylsulfonyl peroxide (DASP) react as components, characterized in that the following steps are performed: a) sulfur trioxide or a solution thereof in a solvent is charged in a high-pressure reactor in a condensed phase; b) a temperature of at least 25° C. (preferably 25° C. to 65° C.) is set; c) the gaseous alkane (e.g. methane) is introduced to the high-pressure reactor until a pressure of at least 10 bar (preferably from 4 MPa (40 bar) to 11 MPa (110 bar)) is reached; d) dialkylsulfonoyl peroxide (DASP) is added; e) after a duration of at least 5 hours (preferably 3 hours to 7 days), the produced raw alkanesulfonic acid (e.g. methanesulfonic acid) is purified in a distillation process comprising at least two steps.

Figure 1:
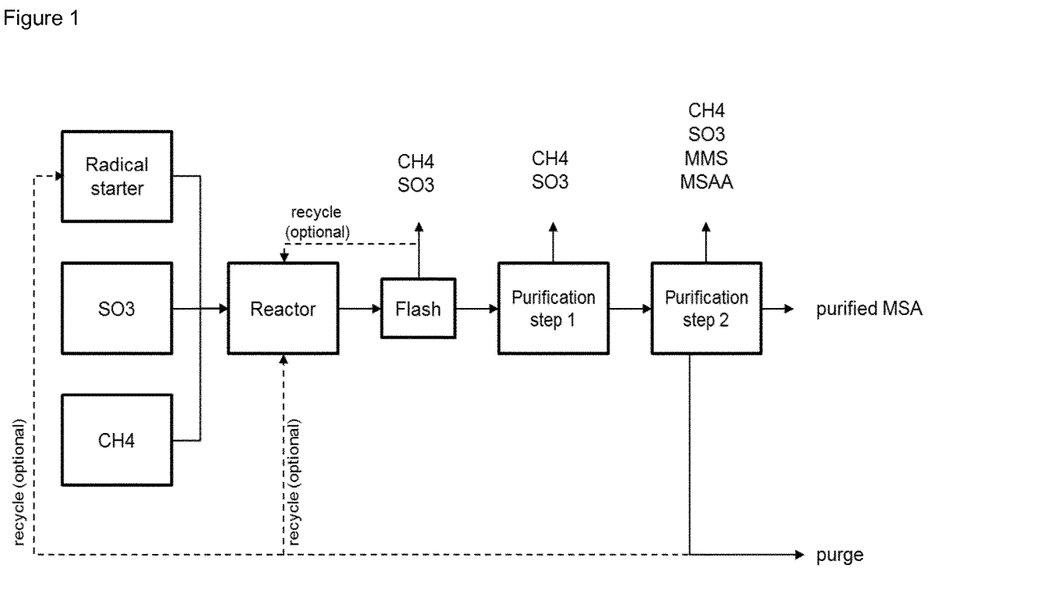
FIG. 1 shows a schematic drawing of an exemplary two-column set-up for the purification of alkanesulfonic acids by distillation according to the invention.

Finally, as mentioned above, FIG. 1 is a schematic illustration of an exemplary layout of the inventive process for the production of alkanesulfonic acids, especially of methanesulfonic acid, including a purification process in at least two steps. FIG. 1 may serve to illustrate some embodiments of the present invention.

As described above FIGS. 2 to 4 are schematic illustrations of some exemplary embodiments of the inventive process for the production of methanesulfonic acid and describe embodiments of this invention in more detail.

EXAMPLES

A. Test of MSA Decomposition and Formation of Methylmethanesulfonate at High Temperatures In the following examples experiments are described focusing on the thermal decomposition of MSA in various mixtures. Results are given as increasing amount of MMS depending on temperature and time. Moreover, in selected cases additional calculations are done on the one hand to determine the formation rate of MMS (formation rate calculated based on MMS formation after 8 h), on the other hand to show the aggregated decomposition rate of MSA to all side products detected in the NMR spectra.

1) Mixture 90 wt-% MSA and 10 wt-% H2SO4 (Solution 1)

MSA (89.95±0.01 g, MSA 99.99 wt. %, contains 72 ppm methyl methanesulfonate, free of water) and sulfuric acid (10.01±0.01 g, $H_2SO_4$ 100%, free of water) were mixed and filled in a round bottom flask equipped with a magnetic stirring bar (glass-lined), a condenser, an internal thermometer and an option to take samples of the mixture. Prior to heating, the system was rendered inert using Argon. Subsequently, the annealing test was carried out at normal pressure and a slight Argon overflow on top of the condenser. Mixtures were exposed to temperatures of 160° C., 180° C., and 200° C., respectively. Samples were taken after 2 h, 4 h, 8 h, 24 h, and 48 h and analyzed by $^1$H-NMR spectroscopy. Results are given in Table 1. Exemplary calculation of formation rate of MMS after 8 h is shown in table 1a.

TABLE 1

Formation of methylmethanesulfonate from MSA under thermal stress (160° C., 180° C. and 200° C., mixture with 90 wt-% MSA and 10 wt-% sulfuric acid)

| | t/h Solution 1 (90 wt. % MSA, 10 wt. % $H_2SO_4$) | | |
|---|---|---|---|
| | 160° C. | 180° C. | 200° C. |
| T= | MMS concentration in wt. % | | |
| 0 | 0.006% | 0.006% | 0.006% |
| 2 | 0.016% | 0.031% | 0.082% |
| 4 | 0.015% | 0.047% | 0.134% |
| 8 | 0.018% | 0.066% | 0.208% |
| 24 | 0.031% | 0.139% | 0.396% |
| 48 | 0.046% | 0.211% | 0.511% |

TABLE 1a

Reaction rate for the formation of methyl methanesulfonate (MMS) given in wt. %/h (mass of MMS at time t related to initial mass of MSA)

| | t/h Solution 1 (90 wt. % MSA, 10 wt. % $H_2SO_4$) | | |
|---|---|---|---|
| | 160° C. | 180° C. | 200° C. |
| T= | (m(MMS, t) − m(MMS, t = 0)/m(initial MSA)/t | | |
| 0 | — | — | — |
| 8 | 0.0015% | 0.0083% | 0.0280% |

To demonstrate how critical overall decomposition of MSA is table 1b shows an exemplary evaluation of the experiments taking into consideration the decomposition of MSA not only to Methylmethanesulfonate but additionally to Methanedisulfonic acid plus Methylbisulfate as derived from the NMR-spectra. The ratio of the decomposition products in this mixture remains constant for all temperatures and time spans and is ca. 60% MMS (corresponding to e.g. 0.511 wt-% MMS after 48 h at 200° C. in table 1), 20% Methylbisulfate and 20% Methanedisulfonic acid.

TABLE 1b

Decomposition of MSA to decomposition products (Methanedisulfonic acid, Methylbisulfate, MMS).

| | t/h Solution 1 (90 wt. % MSA, 10 wt. % $H_2SO_4$) | | |
|---|---|---|---|
| | 160° C. | 180° C. | 200° C. |
| T= | decomposition of MSA in % | | |
| 0 | 0.00% | 0.00% | 0.00% |
| 2 | 0.03% | 0.06% | 0.18% |
| 4 | 0.03% | 0.10% | 0.31% |
| 8 | 0.03% | 0.15% | 0.49% |
| 24 | 0.06% | 0.32% | 0.94% |
| 48 | 0.09% | 0.49% | 1.21% |

2) Mixture 60 wt-% MSA and 40 wt-% Sulfuric Acid (Solution 2)

MSA (60.02±0.01 g, MSA 99.99 wt. %, contains 103 ppm methyl methanesulfonate, free of water) and sulfuric acid (40.03±0.01 g, $H_2SO_4$ 100%, free of water) were mixed and filled in a round bottom flask equipped with a magnetic stirring bar (glass-lined), a condenser, an internal thermometer and an option to take samples of the mixture. Prior to heating, the system was rendered inert using Argon. Subsequently, the annealing test was carried out at normal pressure and a slight Argon overflow on top of the condenser. Mixtures were exposed to temperatures of 160° C., 180° C., and 200° C., respectively. Samples were taken after 2 h, 4 h, 8 h, 24 h, and 48 h and analyzed by $^1$H-NMR spectroscopy. Results are given in Table 2. Exemplary calculation of formation rate of MMS after 8 h is shown in table 2a.

TABLE 2

Formation of methylmethanesulfonate from MSA under thermal stress (160° C., 180° C., 200° C., mixture with 60 wt-% MSA and 40 wt-% sulfuric acid)

| t/h | Solution 2 (60 wt. % MSA, 40 wt. % $H_2SO_4$) | | |
|---|---|---|---|
| T = | 160° C. | 180° C. | 200° C. |
| | MMS concentration in wt. % | | |
| 0 | 0.006 | 0.006 | 0.006 |
| 2 | 0.014 | 0.069 | 0.171 |
| 4 | 0.021 | 0.089 | 0.233 |
| 8 | 0.021 | 0.137 | 0.356 |
| 24 | 0.062 | 0.274 | 0.579 |
| 48 | 0.124 | 0.403 | 0.721 |

TABLE 2a

Reaction rate for the formation of methyl methanesulfonate (MMS) given in wt. %/h (mass of MMS at time t related to initial mass of MSA)

| t/h | Solution 2 (60 wt. % MSA, 40 wt. % $H_2SO_4$) | | |
|---|---|---|---|
| T = | 160° C. | 180° C. | 200° C. |
| | (m(MMS, t)−m(MMS, t = 0)/m(initial MSA)/t | | |
| 0 | — | — | — |
| 8 | 0.0030 wt. %/h | 0.0273 wt. %/h | 0.0728 wt. %/h |

To demonstrate how critical overall decomposition of MSA is table 2b shows an exemplary evaluation of the experiments taking into consideration the decomposition of MSA not only to Methylmethanesulfonate but additionally to Methanedisulfonic acid plus Methylbisulfate as derived from the NMR-spectra. The ratio of the decomposition products in this mixture remains constant for all temperatures and time spans and is ca. 30% MMS (corresponding to e.g. 0.721 wt-% MMS after 48 h at 200° C. in table 2), 45% Methylbisulfate and 25% Methanedisulfonic acid.

TABLE 2b

Decomposition of MSA to decomposition products (MDSA, methyl bisulfate, MMS)

| t/h | Solution 2 (60 wt. % MSA, 40 wt. % $H_2SO_4$) | | |
|---|---|---|---|
| T = | 160° C. | 180° C. | 200° C. |
| | decomposition of MSA in % | | |
| 0 | 0.00% | 0.00% | 0.00% |
| 2 | 0.04% | 0.38% | 1.03% |
| 4 | 0.10% | 0.52% | 1.41% |
| 8 | 0.12% | 0.83% | 2.18% |
| 24 | 0.37% | 1.66% | 3.47% |
| 48 | 0.71% | 2.36% | 4.34% |

3) Mixture Ca. 60 wt-% MSA and 40 wt-% Sulfuric Acid with Potential Side Components as MSAA, $SO_3$ and Marshall's Acid $H_2S_2O_8$ (Solution 3)

MSA (60.04±0.02 g, MSA 99.99 wt. %, contains 72 ppm methyl methanesulfonate, free of water, 180° C. experiment: 103 ppm), sulfuric acid 100% (39.54±0.01 g $H_2SO_4$ 100%, free of water), MSA anhydride (0.31±0.01 g g MSAA, commercial product, 98% purity; purified in a sublimation apparatus at 120° C. and 2 mbar), oleum containing 32 wt. % $SO_3$ (0.69±0.01 g), and $H_2S_2O_8$ (addition of 0.025-0.032 g $H_2O_2$ 70 wt-% aqueous solution; for the reaction of $H_2O_2$ and $H_2O$ with $SO_3$ to $H_2S_2O_8$ and $H_2SO_4$, respectively, corresponding amounts of $SO_3$ were introduced by oleum containing 32 wt. % $SO_3$, $H_2O_2$ as 70 wt. % aqueous solution) were mixed and filled in a round bottom flask equipped with a magnetic stirring bar (glass-lined), a condenser, an internal thermometer and an option to take samples of the mixture. Prior to heating, the system was rendered inert using Argon. Subsequently, the annealing test was carried out at normal pressure and a slight Argon overflow on top of the condenser. Mixtures were exposed to temperatures of 160° C., 180° C., and 200° C., respectively. Samples were taken after 2 h, 4 h, 8 h, 24 h, and 48 h and analyzed by $^1$H-NMR spectroscopy. Results are given in Table 3. Exemplary calculation of formation rate of MMS after 8 h is shown in table 3a. For all annealed samples, peroxides could not be detected.

TABLE 3

Formation of methylmethanesulfonate from MSA under thermal stress (160° C., 180° C., 200° C. mixture with ca. 60 wt-% MSA and 40 wt-% sulfuric acid plus MSAA, $SO_3$, and $H_2S_2O_8$)

| t / h | Solution 3 (59.7 wt. % MSA, 39.8 wt. % $H_2SO_4$, 0.3 wt. % MSA anhydride, 0.1 wt. % $SO_3$, 0.1 wt. % $H_2S_2O_8$) | | |
|---|---|---|---|
| T = | 160° C. | 180° C. | 200° C. |
| | MMS concentration in wt. % | | |
| 0 | 0.004% | 0.006% | 0.004% |
| 2 | 0.007% | 0.089% | 0.130% |
| 4 | 0.019% | 0.144% | 0.193% |
| 8 | 0.036% | 0.206% | 0.241% |
| 24 | 0.089% | 0.371% | 0.460% |
| 48 | 0.156% | 0.494% | 0.605% |

TABLE 3a

Reaction rate for the formation of methyl methanesulfonate (MMS) given in wt. %/h (mass of MMS at time t related to initial mass of MSA)

| t/h | Solution 3 (59.7 wt. % MSA, 39.8 wt. % $H_2SO_4$, 0.3 wt. % MSA anhydride, 0.1 wt. % $SO_3$, 0.1 wt. % $H_2S_2O_8$) | | |
|---|---|---|---|
| T = | 160° C. | 180° C. | 200° C. |
| | (m(MMS, t)-m(MMS, t = 0)/m(initial MSA)/t | | |
| 0 | — | — | — |
| 8 | 0.0067% | 0.0419% | 0.0495% |

To demonstrate how critical overall decomposition of MSA is table 3b shows an exemplary evaluation of the experiments taking into consideration the decomposition of MSA not only to Methylmethanesulfonate but additionally to Methanedisulfonic acid plus Methylbisulfate as derived from the NMR-spectra. The ratio of the decomposition products in this mixture remains constant for all temperatures and time spans and is ca. 30% MMS (corresponding to e.g. 0.605 wt-% MMS after 48 h at 200° C. in table 3), 50% Methylbisulfate and 20% Methanedisulfonic acid.

TABLE 3b

Decomposition of MSA to decomposition products (MDSA, methyl bisulfate, MMS).

| t / h | Solution 3 (59.7 wt. % MSA, 39.8 wt. % $H_2SO_4$, 0.3 wt. % MSA anhydride, 0.1 wt. % $SO_3$, 0.1 wt. % $H_2S_2O_8$) | | |
|---|---|---|---|
| T = | 160° C. | 180° C. | 200° C. |
| | decomposition of MSA in % | | |
| 0 | 0.00% | 0.00% | 0.00% |
| 2 | 0.02% | 0.55% | 0.79% |
| 4 | 0.10% | 0.89% | 1.16% |
| 8 | 0.21% | 1.32% | 1.53% |
| 24 | 0.55% | 2.34% | 2.81% |
| 48 | 0.94% | 3.08% | 3.67% |

4) Mixture 20 wt-% MSA and 80 wt-% Sulfuric Acid (Solution 4)

MSA (20.04±0.04 g MSA 99.99 wt. %, contains 103 ppm methyl methanesulfonate, free of water) and sulfuric acid (80.10±0.14 g $H_2SO_4$ 100%, free of water) were mixed and filled in a round bottom flask equipped with a magnetic stirring bar (glass-lined), a condenser, an internal thermometer and an option to take samples of the mixture. Prior to heating, the system was rendered inert using Argon. Subsequently, the annealing test was carried out at normal pressure and a slight Argon overflow on top of the condenser. Mixtures were exposed to temperatures of 160° C., 180° C., and 200° C., respectively. Samples were taken after 2 h, 4 h, 8 h, 24 h, and 48 h and analyzed by $^1$H-NMR spectroscopy. Results are given in Table 4. Exemplary calculation of formation rate of MMS after 8 h is shown in table 4a.

TABLE 4

Formation of methylmethanesulfonate from MSA under thermal stress (160° C., 180° C., 200° C., mixture with ca. 20 wt-% MSA and 80 wt-% sulfuric acid)

| t/ h | Solution 4 (20 wt. % MSA, 80 wt. % H$_2$SO$_4$) | | |
|---|---|---|---|
| T = | 160° C. | 180° C. | 200° C. |
| | MMS concentration in wt. % | | |
| 0 | 0.002% | 0.002% | 0.002% |
| 2 | 0.009% | 0.046% | 0.091% |
| 4 | 0.016% | 0.071% | 0.128% |
| 8 | 0.023% | 0.103% | 0.182% |
| 24 | 0.055% | 0.148% | 0.232% |
| 48 | 0.069% | 0.176% | 0.291% |

TABLE 4a

Reaction rate for the formation of methyl methanesulfonate (MMS) given in wt. %/h (mass of MMS at time t related to initial mass of MSA)

| t/ h | Solution 4 (20 wt. % MSA, 80 wt. % H$_2$SO$_4$) | | |
|---|---|---|---|
| T = | 160° C. | 180° C. | 200° C. |
| | (m(MMS, t)-m(MMS, t = 0)/m(initial MSA)/t | | |
| 0 | — | — | — |
| 8 | 0.0130% | 0.0630% | 0.1127% |

To demonstrate how critical overall decomposition of MSA is table 4b shows an exemplary evaluation of the experiments taking into consideration the decomposition of MSA not only to Methylmethanesulfonate but additionally to Methanedisulfonic acid plus Methylbisulfate as derived from the NMR-spectra. The ratio of the decomposition products in this mixture remains constant for all temperatures and time spans and is ca. 10% MMS (corresponding to e.g. 0.291 wt-% MMS after 48 h at 200° C. in table 4), 70% Methylbisulfate and 20% Methanedisulfonic acid.

TABLE 4b

Decomposition of MSA to decomposition products (MDSA, methyl bisulfate, MMS).

| t/ h | Solution 4 (20 wt. % MSA, 80 wt. % H$_2$SO$_4$) | | |
|---|---|---|---|
| T = | 160° C. | 180° C. | 200° C. |
| | turnover of MSA in % | | |
| 0 | 0.00% | 0.00% | 0.00% |
| 2 | 0.54% | 2.76% | 5.57% |
| 4 | 0.92% | 3.93% | 7.69% |
| 8 | 1.46% | 5.47% | 10.03% |
| 24 | 2.98% | 8.99% | 14.39% |
| 48 | 4.21% | 10.93% | 16.89% |

Analytics

Unless otherwise described, MSA and samples from annealing experiments were characterized by $^1$H-NMR spectroscopy using a Bruker Avance III HD 400 MHz (C$_6$D$_6$ was used in a capillary as the lock reference). The initial methylmethanesulfonate content of MSA prior to annealing was determined to be 103 ppm (sample 1) and 72 ppm (sample 2) (99.99 wt. % MSA) by $^1$H-NMR spectroscopy. By assigning all $^1$H-NMR non-reference signals in spectra of annealed samples (detected species: MSA, methylmethanesulfonate, methanedisulfonic acid, and methylbisulfate) and subsequent signal integration, quantitative product compositions were derived using the initial MSA mass and underlying reactions for the formation of identified decomposition products. The following signals were used to identify and quantify the substances listed above:

TABLE 5

Positions of $^1$H-NMR signals used to identify and quantify MSA and its decomposition products

| Substance | 1H-NMR* shift [ppm] |
|---|---|
| MSA (H$_3$C—SO$_3$H) | δ($^1$H, CH$_3$) = 3.30-3.43 |
| MSA Anhydride (H$_3$C—SO$_2$—O—SO$_2$—CH$_3$) | δ($^1$H, CH$_3$) = 3.6-3.7 |
| Methylmethanesulfonate (H$_3$C—SO$_2$—O—CH$_3$) | δ($^1$H, OCH$_3$) = 4.06-4.18 |
| | δ($^1$H, SCH$_3$) = 3.21-3.37 |
| Methanedisulfonic Acid (HO—SO$_2$—CH$_2$—SO$_2$OH) | δ($^1$H, CH$_2$) = 5.12-5.12 |
| Methylbisulfate (H$_3$C—O—SO$_2$—OH) | δ($^1$H, CH$_3$) = 4.12-4.23 |

*signals are shifted to lower fields when MSA concentrations increase (lower value: solution 20 wt. % MSA, 80 wt. % H$_2$SO$_4$; higher value: solution 90 wt. % MSA, 10 wt. % H$_2$SO$_4$)

B. Process Simulations Showing Distillation Concepts According to the Invention (Examples) and not Meeting the Scope of this Invention (Comparative Examples)

In the following examples reference compositions for the feed to the distillation ("raw MSA") were chosen which cover a range of raw MSA compositions to be expected according to own experiments and to literature. To develop a distillation concept this raw MSA needs to comprise at least one compound representing the low boilers, at least one compound representing the high boilers and of course the target product MSA. For the process simulations in the following examples MSAA and MMS were selected as low boilers and sulfuric acid was selected as high boiler.

In the process simulation the content of sulfuric acid in the purified MSA was pre-defined (e.g. 10 ppm), other parameters as distillation yield, MSA content of the purified MSA, mass flow and composition of the purge streams, and temperatures at the bottom of the distillation columns were a result of the simulation. As these parameters are not completely independent of one another the following examples target just to show the principle effect of certain parameters in the inventive purification step. A person skilled in the art will be aware that e.g. the yield of the distillation process could be increased, but at the cost of e.g. a higher energy consumption. In the same sense the purity of MSA could be increased, but at the cost of e.g. an increased high boiler purge stream and thus of lower purification yields.

The formation of methylmethanesulfonate or other side products by thermal decomposition of MSA (and/or potential consecutive reactions of the decomposition products) was not integrated in the process simulation in the form of a temperature-dependent reaction. This would have added a huge amount of complexity to the simulation, a complexity which is not needed to show the effect of the current invention. Instead, limits for the residence time of MSA in the distillation step, which are reasonable in an industrial process in combination with the specification requirements for a given product, e.g. for MSA, were defined by the decomposition experiments described above.

In the following examples MSA yields are given as wt-% and calculated as follows:

$$\frac{MSA \text{ in feed [kg/h]} - MSA \text{ in purge [kg/h]}}{MSA \text{ in feed [kg/h]}}$$

discharge with a purity of more than 99.3 wt-%. The impurities in the purified MSA stream are as follows. The content of sulfuric acid is 10 ppm. The content of Methylmethanesulfonate is 48 ppm. The content of MSA anhydride is ca. 0.7 wt-%. The bottom purge amounts to 1300 kg/h and basically consists of sulfuric acid (38.5 wt-%) and MSA (61.5 wt-%). The lights leave the column via the column head (ca. 2 kg/h) and mostly consist of methane, SO3 and Methylmethanesulfonate. The MSA yield is 60.0%, the specific energy consumption in the distillation ca. 0.82 kWh/kg MSA.

Comparative Example 2

Purification of a raw MSA stream produced via reaction of methane and SO3 with a very high content of high boilers is done in a single distillation column. The raw MSA consists of 49.9 wt-% MSA, 49.9 wt-% of sulfuric acid, 0.2 wt-% of MSA anhydride, ca. 100 ppm methylmethanesulfonate, ca. 450 ppm methane and 90 ppm SO3. The total stream contains ca. 2000 kg/h MSA. The distillation is carried out at 203° C. at the bottom of the column and a pressure of 10 mbar at the head of the column. The pressure at the bottom of the column is ca. 20 mbar. The column has a diameter of 1800 mm, the f-factor is 3.3 $Pa^{0.5}$ (theoretical number of trays 12, plus total condenser). The purified MSA leaves the column via side discharge with a purity of ca. 99.4 wt-%. The impurities in the purified MSA stream are as follows. The content of sulfuric acid is 10 ppm. The content of Methylmethanesulfonate is 1 ppm. The content of MSA anhydride is ca. 0.6 wt-%. The bottom purge amounts to 2800 kg/h and basically consists of sulfuric acid (71.5 wt-%)

TABLE 6

Indication on boiling points of selected compounds

| Substance | Boiling point [° C.] | Pressure [bar abs.] | Data source | Remarks |
|---|---|---|---|---|
| CH4 | −161.5 | 1.013 | Gestis[1] | Low boiler |
| SO3 | 44.8 | 1.013 | Gestis[1] | Low boiler |
| MSAA | 69.5 | 0.0053 | Aldrich[2] | Low boiler |
| MMS | 202.5 | 1.013 | Aldrich[2] | Low boiler |
| MSA | 167 | 0.01 | BASF data | Target product |
| Methylbisulfate[3] | >167 | 0.01 | estimate[3] | High boiler |
| Sulfuric acid | 335 | 1.013 | Gestis[1] | High boiler |
| Methionic acid | 200 | 0.01 | BASF data | High boiler |

[1]Gestis Stoffdatenbank, link: http://www.dguv.de/ifa/gestis/gestis-stoffdatenbank/index.jsp
[2]Aldrich, Katalog Handbuch Feinchemikalien 1999-2000, Deutschland
[3]No date on individual boiling point found in literature. Classification as high boiler since Methylbisulfate has a molecular composition similar to MSA but a higher molecular weight.

Comparative Example 1

Purification of a raw MSA stream produced via reaction of methane and SO3 with a significant content of high boilers is done in a single distillation column. The raw MSA consists of 79.7 wt-% MSA, 19.9 wt-% of sulfuric acid, 0.3 wt-% of MSA anhydride, ca. 159 ppm methylmethanesulfonate, ca. 460 ppm methane and 90 ppm SO3. The total stream contains ca. 2000 kg/h MSA. The operational parameters of the distillation were selected so that the sulfuric acid content in the purified MSA was 10 ppm.

The distillation is carried out at 192° C. at the bottom of the column and a pressure of 10 mbar at the head of the column. The pressure at the bottom of the column is ca. 20 mbar. The column has a diameter of 1800 mm, the f-factor is 2.4 $Pa^{0.5}$ (theoretical number of trays 12, plus total condenser). The purified MSA leaves the column via side and MSA (28.5 wt-%). The lights leave the column via the column head (ca. 2 kg/h) and mostly consist of methane, SO3 and Methylmethanesulfonate. The MSA yield is 60.0%, the specific energy consumption in the distillation ca. 2.33 kWh/kg MSA.

The high amounts of high boilers (sulfuric acid) apparently render the purification of MSA much more challenging and a simple set-up as applied for the removal of small amounts of high boilers as applied for aqueous synthesis routes for MSA does not meet the requirements when the distillation feed contains a high amount of sulfuric acid. An acceptable sulfuric acid content is difficult to achieve in a single column distillation set-up while at the same time achieving reasonable yields and keeping the decomposition of MSA to side products low.

Example 1

Figure 2:
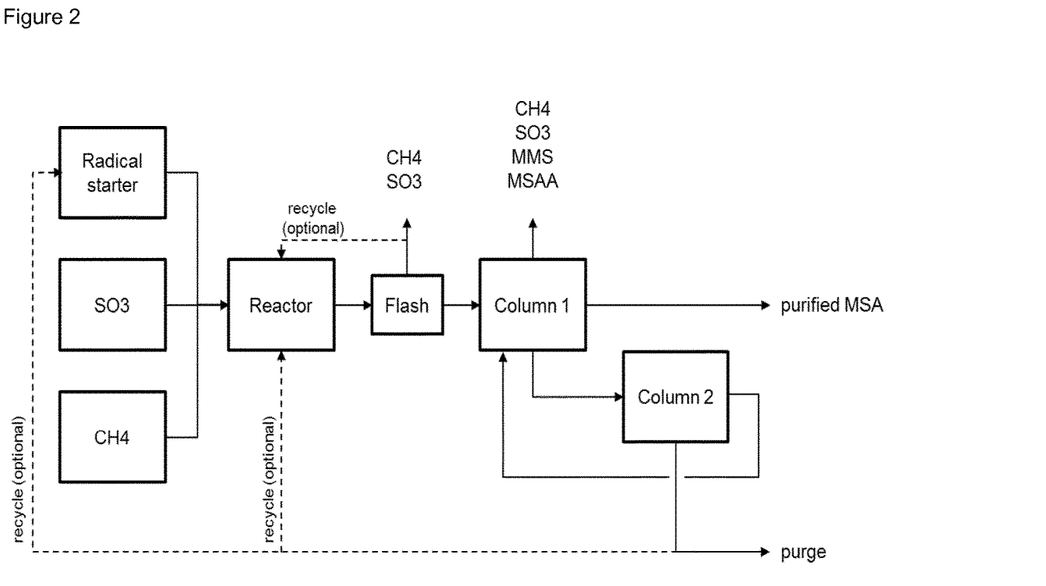
FIG. 2 shows a schematic drawing of a two-column set-up for the purification of alkanesulfonic acids by distillation according to the invention, which is particularly suitable for the purification of MSA.

Raw MSA from the reaction of methane and SO3 was purified in a two-column set-up as shown in FIG. 2. The raw MSA consisted of 78.8 wt-% MSA, 20.0 wt-% sulfuric acid, 0.2 wt-% MSA anhydride, 0.1 wt-% methane and ca. 160 ppm methylmethanesulfonate. The MSA mass flow was 2000 kg/h. The raw MSA was sent to the distillation after depressurizing the mixture from a pressure in the synthesis unit of ca. 100 bar to 1 bar in a flash unit.

In a first distillation step (column 1), light boilers are removed from raw MSA at the top of the column (ca. 30 kg/h) and purified MSA is removed via side discharge ($T_{MSA}$ at discharge 163° C.). In the second distillation step (column 2) MSA is depleted of high boilers, especially of sulfuric acid. One fraction of the high boilers is purged from the second column via a discharge line at the bottom (purge: 643 kg/h, 21.1 wt-% MSA, 78.9 wt-% sulfuric acid), the rest is returned to column 1.

Column 1 is operated at a pressure of 10 mbar at the head of the column and 20 mbar at the bottom of the column (gas phase above sump), the temperature at the bottom of the column is 198° C. The column has a diameter of 1700 mm, the f-factor is 1.9 $Pa^{0.5}$ (theoretical number of trays 12, plus partial condenser). Column 2 is operated with a pressure of 10 mbar at the head of the column (practically no pressure drop as no column internals), the temperature at the bottom of the column is 188° C. The column has a diameter of 2400 mm, the f-factor is 0.45 $Pa^{0.5}$ (theoretical number of trays 2, plus total condenser). The energy required to evaporate the raw MSA in column 1 was provided by a heat exchanger ("Zwangsumlaufverdampfer") connected to the bottom of column 1 and circulated by a pump. The same applies for the set-up of column 2.

MSA was obtained with a yield of 93.2%, the resulting MSA had a purity of 99.7 wt-%. The impurities in the purified MSA stream are as follows. The content of sulfuric acid is 10 ppm. The content of Methylmethanesulfonate is 7 ppm. The content of MSA anhydride is ca. 0.3 wt-%. The specific energy consumption for the evaporation is 0.47 kWh/kg MSA (evaporation energy only, no condensation energy, no pumping energy).

Example 2

The same set-up as in example 1 was used. However, the feed composition to the distillation had a higher sulfuric acid content as follows: 49.7 wt-% MSA, 50.0 wt-% sulfuric acid, 0.2 wt-% MSA anhydride, 0.1 wt-% methane and ca. 100 ppm methylmethanesulfonate. The MSA mass flow was 2000 kg/h.

In a first distillation step (column 1), light boilers are removed from raw MSA at the top of the column (10 kg/h) and purified MSA is removed via side discharge ($T_{MSA}$ at discharge 164° C.). One fraction of the high boilers is purged from the second column via a discharge line at the bottom (purge: 2367 kg/h, 15 wt-% MSA, 85 wt-% sulfuric acid), the rest is returned to column 1.

Column 1 is operated at a pressure of 10 mbar at the head of the column and 20 mbar at the bottom of the column (gas phase above sump), the temperature at the bottom of the column is 198° C. The column has a diameter of 2000 mm, the f-factor is 1.9 $Pa^{0.5}$ (theoretical number of trays 12, plus partial condenser). Column 2 is operated with a pressure of 10 mbar at the head of the column (practically no pressure drop as no column internals), the temperature at the bottom of the column is 189° C. The column has a diameter of 3000 mm, the f-factor is 3.1 $Pa^{0.5}$ (theoretical number of trays 2, plus partial condenser).

MSA was obtained with a yield of 82.2%, the resulting MSA had a purity of 99.5 wt-%. The impurities in the purified MSA stream are as follows. The content of sulfuric acid is 10 ppm. The content of Methylmethanesulfonate is 7 ppm. The content of MSA anhydride is ca. 0.5 wt-%. The specific energy consumption for the evaporation is 2.02 kWh/kg MSA (evaporation energy only, no condensation energy, no pumping energy).

Example 3

The same set-up and a comparable feed composition as in example 1 was used: 78.8 wt-% MSA, 20.0 wt-% sulfuric acid, 0.2 wt-% MSA anhydride, 1.0 wt-% methane and ca. 160 ppm methylmethanesulfonate. The MSA mass flow was 2000 kg/h. Operating conditions were modified in a way, that the resulting MSA had a sulfuric acid content of 30 ppm.

In a first distillation step (column 1), light boilers are removed from raw MSA at the top of the column (30 kg/h) and purified MSA is removed via side discharge ($T_{MSA}$ at discharge 163° C.). One fraction of the high boilers is purged from the second column via a discharge line at the bottom (purge: 643 kg/h, 21.1 wt-% MSA, 78.9 wt-% sulfuric acid), the rest is returned to column 1.

Column 1 is operated at a pressure of 10 mbar at the head of the column and 20 mbar at the bottom of the column (gas phase above sump), the temperature at the bottom of the column is 198° C. The column has a diameter of 1700 mm, the f-factor is 1.8 $Pa^{0.5}$ (theoretical number of trays 12, plus partial condenser). Column 2 is operated with a pressure of 10 mbar at the head of the column (practically no pressure drop as no column internals), the temperature at the bottom of the column is 188° C. The column has a diameter of 2400 mm, the f-factor is 0.45 $Pa^{0.5}$ (theoretical number of trays 2, plus partial condenser).

MSA was obtained with a yield of 93.2%, the resulting MSA had a purity of 99.7 wt-%. The impurities in the purified MSA stream are as follows. The content of sulfuric acid is 30 ppm. The content of Methylmethanesulfonate is 20 ppm. The content of MSA anhydride is ca. 0.3 wt-%. The specific energy consumption for the evaporation is 0.46 kWh/kg MSA (evaporation energy only, no condensation energy, no pumping energy).

Example 4

Figure 3:
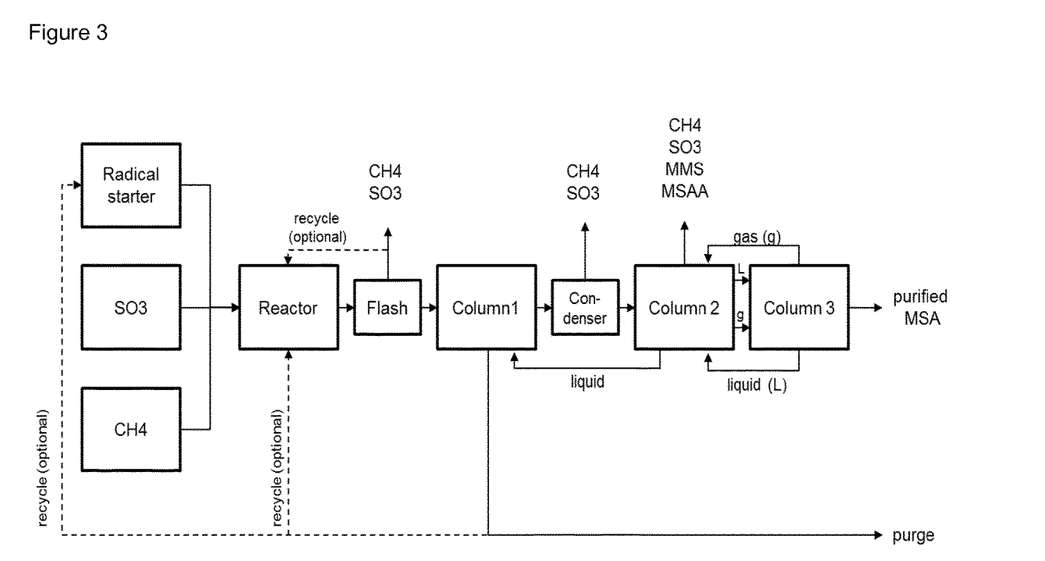
FIGS. 3 and 4 show schematic drawings of exemplary three-column set-ups for the purification of alkanesulfonic acids by distillation according to the invention.

A raw MSA stream from the reaction of methane and SO3 was purified in a three-column set-up as shown in FIG. 3, columns 2 and 3 are operated in a dividing wall set-up. The raw MSA stream consisted of 78.5 wt-% MSA, 21.0 wt-% sulfuric acid, 0.3 wt-% MSA anhydride, 0.2 wt-% methane and ca. 157 ppm methylmethanesulfonate. The MSA mass flow was 2000 kg/h. The raw MSA was sent to the distillation after depressurizing the mixture from a pressure in the synthesis unit of ca. 100 bar to 1 bar in a flash unit.

In a first distillation step, a falling film evaporator was operated at a pressure of 10 mbar at head and bottom of the vessel (no packings or other typical column internals generating pressure drop) and a bottom temperature of 183° C. The column has a diameter of 1600 mm, the f-factor is 1.6 $Pa^{0.5}$ (theoretical number of trays 3. The gas stream leaving the falling film evaporator at the head basically contains MSA mostly depleted of sulfuric acid but not meeting the required specification yet (composition ca. 4 wt-% sulfuric acid and 96 wt-% MSA, temperature condenser 135° C.). A purge stream left the falling film evaporator at the bottom. This bottom purge of 840 kg/h consisted of 63.4 wt-% sulfuric acid, 36.6 wt-% MSA and traces (<0.1 wt-%) of MSA anhydride and high boilers.

The gas stream leaving the falling film evaporator at the head was condensed, low boilers were purged from the system (ca. 20 kg/h in total containing e.g. Methylmethanesulfonate, MSA anhydride, methane, SO3 and MSA) and the high boilers were sent to column 2 which was closely connected to column 3 (separating wall set-up of two columns, column 3 has no internals). The energy required to evaporate the raw MSA depleted of some sulfuric acid and some light boilers in column 2 was provided by a heat exchanger ("Zwangsumlaufverdampfer") connected to the bottom of column 2 and circulated by a pump. The finally purified MSA left column 3 via side discharge.

MSA at the upper part of column 2 was depleted of sulfuric acid further and ca. 2750 kg/h of this pre-purified MSA left column 2 via side discharge to the upper part of column 3. From a side discharge at the lower part of column 2 ca. 1900 kg/h of a pre-purified MSA gas stream were sent to the lower part of column 3. From the bottom of column 3 ca. 360 kg/h mainly consisting of MSA were sent back to the lower part of column 2. From the head of column 3 ca. 2520 kg/h mainly consisting of MSA were sent back to the upper part of column 2. 1680 kg/h of finally purified MSA were removed from column 3 via side discharge.

Column 2 was operated at a bottom temperature of 182° C., a pressure at the head of the column of 10 mbar and a pressure at the bottom of the column (gas phase above sump) of 20 mbar. Column 3 was operated at a bottom temperature of 171° C., and a pressure at head and bottom (i.e. gas phase above sump) of the column of 15 mbar as this column has no packings or other internals which create pressure drop. Column 2 has a diameter of 1700 mm, the f-factor is 1.2 $Pa^{0.5}$ (theoretical number of trays 12, plus total condenser). Column 3 has a diameter of 1400 mm, the f-factor is 1.7 $Pa^{0.5}$ (theoretical number of trays 10).

The resulting MSA had a purity of 99.9 wt-%. The impurities in the purified MSA stream are as follows. The content of sulfuric acid is 10 ppm. The content of Methylmethanesulfonate is 5 ppm. The content of MSA anhydride is ca. 0.1 wt-%. The MSA yield is 84.0%, the specific energy consumption in the distillation ca. 0.55 kWh/kg MSA.

Due to the lack of internals in columns 1 and 3, high circulation rates of the mixtures in the column sumps and minimized column volumes, the residence time of MSA in the purification step is minimized, the temperature stress on MSA kept to a minimum and the formation of Methylmethanesulfonate reduced. This set-up also allows to keep the temperatures at the bottom of the columns below 200° C. which helps to suppress Methylmethanesulfonate formation and is beneficial for the material of construction. The MSA yield is high and the purity of the products meets market standards.

Example 5

The same three-column set-up as in example 4 was used. The raw MSA consisted of 49.8 wt-% MSA, 49.8 wt-% sulfuric acid, 0.2 wt-% MSA anhydride, 0.1 wt-% methane and ca. 100 ppm methylmethanesulfonate. The MSA mass flow was 2000 kg/h. The raw MSA was sent to the distillation after depressurizing the mixture from a pressure in the synthesis unit of ca. 100 bar to 1 bar in a flash unit.

The falling film evaporator was operated at a pressure of 10 mbar at head and bottom of the vessel (no packings or other typical column internals generating pressure drop) and a bottom temperature of 189° C. The column has a diameter of 3600 mm, the f-factor is 1.9 $Pa^{0.5}$ (theoretical number of trays 3). The gas stream leaving the falling film evaporator at the head basically contains MSA mostly depleted of sulfuric acid but not meeting the required specification yet (composition ca. 13 wt-% sulfuric acid and 87 wt-% MSA, temperature condenser 135° C.). A purge stream left the falling film evaporator at the bottom. This bottom purge of 2315 kg/h consisted of 86.4 wt-% sulfuric acid, 13.6 wt-% MSA and traces (<0.1 wt-%) of MSA anhydride and high boilers.

A steam of light boilers is purged from the system after condensation prior to column 2 (ca. 15 kg/h in total containing e.g. Methylmethanesulfonate, MSA anhydride, methane, SO3 and MSA). MSA at the upper part of column 2 was depleted of sulfuric acid further and ca. 2790 kg/h of this pre-purified MSA left column 2 via side discharge to the upper part of column 3. From a side discharge at the lower part of column 2 ca. 1900 kg/h of a pre-purified MSA gas stream were sent to the lower part of column 3. From the bottom of column 3 ca. 370 kg/h mainly consisting of MSA were sent back to the lower part of column 2. From the head of column 3 ca. 2640 kg/h mainly consisting of MSA were sent back to the upper part of column 2. 1678 kg/h of finally purified MSA were removed from column 3 via side discharge.

Column 2 was operated at a bottom temperature of 182° C., a pressure at the head of the column of 10 mbar and a pressure at the bottom of the column (gas phase above sump) of 20 mbar. Column 3 was operated at a bottom temperature of 171° C., and a pressure at head and bottom (i.e. gas phase above sump) of the column of 15 mbar as this column has no packings or other internals which create pressure drop. Column 2 has a diameter of 1700 mm, the f-factor is 1.1 $Pa^{0.5}$ (theoretical number of trays 12, plus total condenser). Column 3 has a diameter of 1400 mm, the f-factor is 1.7 $Pa^{0.5}$ (theoretical number of trays 10).

The resulting MSA had a purity of 99.9 wt-%. The impurities in the purified MSA stream are as follows. The content of sulfuric acid is 10 ppm. The content of Methylmethanesulfonate is 6 ppm. The content of MSA anhydride is ca. 0.1 wt-%. The MSA yield is 83.8%, the specific energy consumption in the distillation ca. 1.55 kWh/kg MSA.

Example 6

Figure 4:
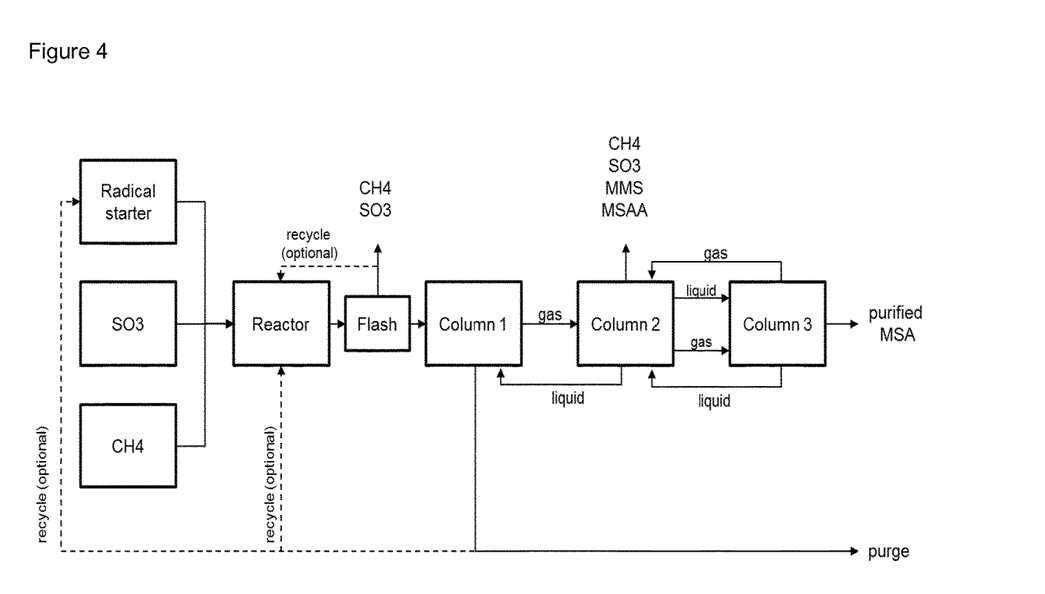

The same three-column set-up as in example 4 was used but without the additional condensation step after column 1 as shown in FIG. 4. The raw MSA consisted of 78.6 wt-% MSA, 20.9 wt-% sulfuric acid, 0.3 wt-% MSA anhydride, 0.2 wt-% methane and ca. 157 ppm methylmethanesulfonate. The MSA mass flow was 2000 kg/h. The raw MSA was sent to the distillation after depressurizing the mixture from a pressure in the synthesis unit of ca. 100 bar to 1 bar in a flash unit.

The falling film evaporator was operated at a pressure of 20 mbar at head and bottom of the vessel (no packings or other typical column internals generating pressure drop) and a bottom temperature of 198° C. The column has a diameter of 1700 mm, the f-factor is 1.2 $Pa^{0.5}$ (theoretical number of trays 3). The gas stream leaving the falling film evaporator at the head basically contains MSA mostly depleted of sulfuric acid but not meeting the required specification yet (composition ca. 4 wt-% sulfuric acid and 96 wt-% MSA, temperature condenser 135° C.). A purge stream left the falling film evaporator at the bottom. This bottom purge of 902 kg/h consisted of 59.0 wt-% sulfuric acid, 41.0 wt-% MSA and traces (<0.1 wt-%) of MSA anhydride and high boilers.

A steam of light boilers is purged from the system at the head of column 2 (ca. 10 kg/h in total containing e.g. Methylmethanesulfonate, MSA anhydride, methane, SO3 and MSA). MSA at the upper part of column 2 was depleted of sulfuric acid further and ca. 2940 kg/h of this pre-purified MSA left column 2 via side discharge to the upper part of column 3. From a side discharge at the lower part of column 2 ca. 1890 kg/h of a pre-purified MSA gas stream were sent to the lower part of column 3. From the bottom of column 3 ca. 500 kg/h mainly consisting of MSA were sent back to the lower part of column 2. From the head of column 3 ca. 2690 kg/h mainly consisting of MSA were sent back to the upper part of column 2. 1638 kg/h of finally purified MSA were removed from column 3 via side discharge.

Column 2 was operated at a bottom temperature of 186° C., a pressure at the head of the column of 10 mbar and a pressure at the bottom of the column (gas phase above sump) of 20 mbar. Column 3 was operated at a bottom temperature of 171° C., and a pressure at head and bottom (i.e. gas phase above sump) of the column of 15 mbar as this column has no packings or other internals which create pressure drop. Column 2 has a diameter of 1700 mm, the f-factor is 1.3 $Pa^{0.5}$ (theoretical number of trays 12, plus total condenser). Column 3 has a diameter of 1500 mm, the f-factor is 1.5 $Pa^{0.5}$ (theoretical number of trays 10).

The resulting MSA had a purity of 99.5 wt-%. The impurities in the purified MSA stream are as follows. The impurities in the purified MSA stream are as follows. The content of sulfuric acid is 10 ppm. The content of Methylmethanesulfonate is 49 ppm. The content of MSA anhydride is ca. 0.5 wt-%. The MSA yield is 81.5%, the specific energy consumption in the distillation ca. 0.28 kWh/kg MSA.

TABLE 7a

Summary of the examples with an MSA content of ca. 80 wt-% (selected parameters)

|  | Comp. Ex. 1 | Ex. 1 | Ex. 3 | Ex. 4 | Ex. 6 |
|---|---|---|---|---|---|
| Number of columns | 1 | 2 | 2 | 3 | 3 |
| Condensation step | — | — | — | yes | no |
| Feed to distillation (selected compounds, rest see examples) | | | | | |
| MSA [wt-%] | 79.7 | 78.8 | 78.8 | 78.5 | 78.6 |
| H2SO4 [wt-%] | 19.9 | 20.0 | 20.0 | 21.0 | 20.9 |
| MMS [ppm] | 159 | 160 | 160 | 157 | 157 |
| MSA [kg/h] | 2000 | 2000 | 2000 | 2000 | 2000 |
| Total feed to dist. [kg/h] | 2510 | 2538 | 2538 | 2548 | 2545 |
| Column operation | | | | | |
| Bottom T, column 1 [° C.] | 192 | 198 | 198 | 183 | 198 |
| Bottom T, column 2 [° C.] | — | 188 | 188 | 182 | 186 |
| Bottom T, column 3 [° C.] | — | — | — | 171 | 171 |
| Max pressure above sump [mbar abs] | 20 | 20 | 20 | 20 | 20 |
| Distillation performance | | | | | |
| MSA yield [wt-%] | 60 | 93.2 | 93.2 | 84 | 81.5 |
| Energy demand for evaporation [kW] | 988 | 881 | 857 | 919 | 455 |
| High boiler purge [kg/h] | 1300 | 643 | 643 | 840 | 902 |
| MSA content in purge [%] | 61.5 | 21.1 | 21.1 | 36.6 | 41 |
| MSA in purge [kg/h] | 800 | 136 | 136 | 307 | 370 |
| Purified MSA [kg/h] | 1210 | 1864 | 1864 | 1680 | 1638 |
| Specific energy consumption [kWh/kg MSA] | 0.82 | 0.47 | 0.46 | 0.55 | 0.28 |
| Product quality | | | | | |
| MSA purity [wt-%] | 99.3 | 99.7 | 99.7 | 99.9 | 99.5 |
| H2SO4 in MSA [ppm] | 10 | 10 | 30 | 10 | 10 |
| MMS in MSA [ppm] | 48 | 7 | 20 | 5 | 49 |

TABLE 7b

Summary of the examples with an MSA content of ca. 50 wt-% (selected parameters)

|  | Comp. Ex. 2 | Ex. 2 | Ex. 5 |
|---|---|---|---|
| Number of columns | 1 | 2 | 3 |
| Condensation step | — | — | yes |
| Feed to distillation (selected compounds, rest see examples) | | | |
| MSA [wt-%] | 49.9 | 49.7 | 49.8 |
| H2SO4 [wt-%] | 49.9 | 50.0 | 49.8 |
| MMS [ppm] | 100 | 100 | 100 |
| MSA [kg/h] | 2000 | 2000 | 2000 |
| Total feed to dist. [kg/h] | 4011 | 4024 | 4014 |

TABLE 7b-continued

Summary of the examples with an MSA content of ca. 50 wt-% (selected parameters)

|  | Comp. Ex. 2 | Ex. 2 | Ex. 5 |
|---|---|---|---|
| Column operation | | | |
| Bottom T, column 1 [° C.] | 203 | 198 | 189 |
| Bottom T, column 2 [° C.] | — | 189 | 182 |
| Bottom T, column 3 [° C.] | — | — | 171 |
| Max pressure above sump [mbar abs] | 20 | 20 | 20 |
| Distillation performance | | | |
| MSA yield [wt-%] | 60 | 82.2 | 83.8 |
| Energy demand for evaporization [kW] | 2822 | 3317 | 2602 |
| High boiler purge [kg/h] | 2800 | 2367 | 2315 |
| MSA content in purge [%] | 28.5 | 15 | 13.6 |
| MSA in purge [kg/h] | 798 | 355 | 315 |
| Purified MSA [kg/h] | 1210 | 1644 | 1678 |
| Specific energy consumption [kWh/kg MSA] | 2.33 | 2.02 | 1.55 |
| Product quality | | | |
| MSA purity [wt-%] | 99.4 | 99.5 | 99.9 |
| H2SO4 in MSA [ppm] | 10 | 10 | 10 |
| MMS in MSA [ppm] | 1 | 7 | 6 |

Tables 7a and 7b show that both a distillation set-up with one column (comparative example) and set-ups with at least two columns (inventive examples) good MSA purities can be achieved, but in a single-column set-up this can only be achieved by drastically increasing the high boiler purge and consequently very poor MSA yields. When trying to increase the yield in a single-column set-up the only way is to significantly reduce the purge and to increase the temperature. However, the immediate consequence is a drastic increase in MSA decomposition as can be seen in the decomposition experiments in section A.

The resulting residence times of MSA in the hold-up can be estimated as follows. Typical volumes of a hold-up per column could be in the range of 1 to 10 tons, the larger the hold-up the more the decomposition will proceed. For the following examples two hold-ups being in this range were used and the resulting decomposition rates estimated, namely for 2000 kg and for 5000 kg MSA. The residence time e.g. in comparative example 1 then calculates as Hold-up $MSA = 2000$ kg (volume of hold-up) × 61, 5 wt-%($conc.$ of MSA in purge = $conc.$ at the bottom of the column) =

$$1230 \text{ kg}$$

Residence time MSA at the bottom of the column =

1230 kg ($MSA$ in hold-up)/2000 kg/h ($MSA$ in feed to column) = 0, 62 h

In the following tables 8a and 8b the residence times of MSA are calculated accordingly for exemplary MSA hold-ups of (i) 2000 kg and for (ii) 5000 kg.

TABLE 8a

Residence time of MSA at the bottom of the column for different hold-ups and an MSA content of ca. 80 wt-%

|  | Comp. Ex. 1 | Ex. 1 | Ex. 3 | Ex. 4 | Ex. 6 |
|---|---|---|---|---|---|
| kg MSA in Hold-up | 1230 | 422 | 422 | 732 | 820 |
| kg MSA in Hold-up | 3075 | 1055 | 1055 | 1830 | 2050 |
| Residence time MSA [h] | 0.62 | 0.21 | 0.21 | 0.37 | 0.41 |
| Residence time MSA [h] | 1.54 | 0.53 | 0.53 | 0.92 | 1.03 |

TABLE 8b

Residence time of MSA at the bottom of the column for different hold-ups and of ca. 50 wt-%

|  | Comp. Ex. 2 | Ex. 2 | Ex. 5 |
|---|---|---|---|
| kg MSA in Hold-up | 570 | 300 | 272 |
| kg MSA in Hold-up | 1425 | 750 | 680 |
| Residence time MSA [h] | 0.29 | 0.15 | 0.14 |
| Residence time MSA [h] | 0.71 | 0.38 | 0.34 |

This invention offers measures how to keep temperatures in the column low while at the same time achieving high MSA yields rendering MSA with a high purity, namely a low sulfate content and a low MMS content.

Finally, the following text passages describe processes and measures in the surrounding field of the present invention:

A process for preparing alkanesulfonic acids from sulfur trioxide and an alkane, wherein the produced raw alkane sulfonic acid is purified in a distillation process comprising at least two stages.

A process as described above, wherein the alkanesulfonic acid is methanesulfonic acid (MSA) and wherein the alkane is methane.

Process as described above, wherein said distillation process comprising at least two distillation stages comprises a first distillation stage at a temperature in the range of 30° to 150° C., preferably 50° to 130° C. and a subsequent second distillation stage at a temperature in the range of 150° to 240° C., preferably 160° to 200° C.

Process as described above, wherein said distillation process comprising at least two distillation stages comprises a first distillation stage at a pressure in the range of 100 to 1000 mbar, preferably 200 to 800 mbar and a subsequent second distillation stage at a pressure in the range of 0.1 to 20 mbar, preferably 2 to 10 mbar.

Process as described above, wherein said distillation process comprising at least two distillation stages is performed in at least two separate distillation columns, preferably in two separate distillation columns.

Process as described above, wherein the first distillation stage is performed in a reaction vessel and the second distillation stage is performed in a distillation column or a set of columns.

Process as described above, wherein said distillation process comprising at least two distillation stages involves stripping of the distillation mixture with an inert gas in the first distillation stage.

Process as described above, wherein said distillation process comprising at least two distillation stages involves stripping of the distillation mixture with an inert gas in the first distillation stage, selected from the list consisting of nitrogen and argon.

Process as described above, wherein the alkanesulfonic acid is withdrawn at the side discharge of the distillation column in the second distillation stage and also of the columns of potential further columns.

Process as described above, wherein the process is a continuous process.

Process as described above, wherein at least a part of the bottom fraction of the MSA distillation in column 2 and/or additional downstream columns is not purged from the system but at least partially recycled to the synthesis step of the radical starter solution or to the synthesis step of the MSA synthesis with $CH_4$ and $SO_3$.

A process for purifying reaction mixtures comprising raw alkanesulfonic acids, preferably raw methanesulfonic acid, by subjecting the reaction mixture to at least two distillation stages.

Alkanesulfonic acid, preferably methanesulfonic acid, obtainable by the processes as described above.

Use of an alkanesulfonic acid, preferably methanesulfonic acid, obtainable by the processes as described above, for cleaning applications or in an electroplating process.

The invention claimed is:

1. A process for preparing an alkanesulfonic acid, the process comprising:

reacting sulfur trioxide and an alkane to obtain a raw alkane sulfonic acid; and purifying the raw alkane sulfonic acid in a distillation process comprising at least two steps, to obtain a purified alkanesulfonic acid, wherein a ratio of an inner column diameter in a sump and an inner column diameter of the column directly above the sump for each column in the distillation process is in the range from 0.20 to 0.99.

2. The process according to claim 1, wherein the distillation process employs a distillation set-up comprising (i) one distillation column with high separation performance (main distillation), and (ii) at least one additional distillation column, either before and/or after the main distillation column, each with a separation performance not matching that of the main distillation column (pre-distillation and/or post-distillation, respectively).

3. The process according to claim 1, wherein the alkanesulfonic acid is methanesulfonic acid (MSA) and the alkane is methane.

4. The process according to claim 1, wherein the distillation process is operated at a temperature in the range of 130° C. to 200° C. in all distillation columns.

5. The process according to claim 1, wherein the distillation process is operated at a pressure in the range of 0.1 to 30 mbar in all distillation columns.

6. The process according to claim 1, wherein the distillation process is performed in at least two separate distillation columns.

7. The process according to claim 1, wherein the distillation process consists of two or three separate distillation columns.

8. The process according to claim 1, wherein the distillation process occurs such that each distillation step is carried out in one column or in more than one column operated in parallel.

9. The process according to claim 1, wherein a first distillation step, a third distillation step, or both is performed in a reaction vessel, and a second distillation step is performed in a distillation column or in a set of columns.

10. The process according to claim 1, wherein the distillation process comprises stripping of a distillation mixture with an inert gas in at least one of the distillation steps.

11. The process according to claim 1, wherein the distillation process comprises stripping of a distillation mixture with an inert gas in a first distillation step, such that the inert gas is selected from the group consisting of nitrogen and argon.

12. The process according to claim 1, wherein the alkanesulfonic acid is withdrawn at a side discharge of a first column in a two-column set-up, or at a side discharge of a third column of a three-column set-up.

13. The process according to claim 1, wherein the process is a continuous process.

14. The process according to claim 1, wherein the process is water-free.

15. The process according to claim 1, wherein the alkanesulfonic acid yield in the distillation process is above 70% by weight.

16. The process according to claim 1, wherein at least a part of a bottom fraction of the distillation process is not purged from the system but at least partially recycled to a reacting step of a radical starter solution or to the reacting step to obtain the raw alkane sulfonic acid.

17. The process according to claim 1, wherein a main distillation column is operated at a higher pressure drop than all other column or columns in the distillation process.

18. The process according to claim 1, wherein:

the alkanesulfonic acid is methane sulfonic acid; and at least one of the following is satisfied:
- a sulfate content of the purified methane sulfonic acid is less than 100 ppm,
- an MMS content of the purified methane sulfonic acid is less than 1000 ppm, and
- a yield of the purified methane sulfonic acid in the distillation process is above 80 wt-%.

19. The process according to claim 1, wherein a residence time in each distillation column of the distillation process is less than 5 h.

20. The process according to claim 1, wherein accumulation of peroxides in the distillation process, in the purified alkanesulfonic acid, or both, is prevented in the distillation process by operating the distillation process at temperatures in the range from 130° C. to 200° C., at pressures in the range from 0.1 mbar to 30 mbar, and with residence times at the bottom of each column of less than 5 h.

21. The process according to claim 1, wherein the raw alkanesulfonic acid is sent to an expansion vessel prior to entering the distillation process.

22. A process, comprising performing a chemical synthesis or an electroplating process with a purified alkanesulfonic acid obtained in the process of claim 1.

23. A process for preparing an alkanesulfonic acid, the process comprising:
- reacting sulfur trioxide and an alkane to obtain a raw alkane sulfonic acid; and
- purifying the raw alkane sulfonic acid in a distillation process comprising at least two steps, to obtain a purified alkanesulfonic acid,
- wherein the distillation process comprises stripping of a distillation mixture with an inert gas in at least one of the distillation steps.

24. A process for preparing an alkanesulfonic acid, the process comprising:
- reacting sulfur trioxide and an alkane to obtain a raw alkane sulfonic acid; and
- purifying the raw alkane sulfonic acid in a distillation process comprising at least two steps, to obtain a purified alkanesulfonic acid,
- wherein the process is water-free.

* * * * *